United States Patent [19]

Teraji et al.

[11] Patent Number: 4,521,413

[45] Date of Patent: * Jun. 4, 1985

[54] CEPHEM COMPOUNDS

[75] Inventors: Tsutomu Teraji, Osaka; Kazuo Sakane, Amagasaki; Jiro Goto, Suita, all of Japan

[73] Assignee: Fujisawa Pharmaceutical Co., Ltd., Osaka, Japan

[ * ] Notice: The portion of the term of this patent subsequent to Apr. 26, 2000 has been disclaimed.

[21] Appl. No.: 414,471

[22] Filed: Sep. 2, 1982

[30] Foreign Application Priority Data

Sep. 14, 1981 [GB] United Kingdom ............... 8127663
Dec. 14, 1981 [GB] United Kingdom ............... 8137680
Jul. 1, 1982 [GB] United Kingdom ............... 8218982

[51] Int. Cl.$^3$ ................. C07D 501/38; A61K 31/545
[52] U.S. Cl. ...................................... 514/203; 544/25
[58] Field of Search ................. 544/27, 25, 21, 26; 424/246

[56] References Cited

U.S. PATENT DOCUMENTS

| | | | |
|---|---|---|---|
| 4,200,746 | 4/1980 | Gok et al. | 544/25 |
| 4,252,802 | 2/1981 | Dengel et al. | 544/25 |
| 4,268,509 | 5/1981 | Teraji et al. | 424/246 |
| 4,381,299 | 4/1983 | Teraji et al. | 544/25 |
| 4,431,642 | 2/1984 | Teraji et al. | 544/27 |

FOREIGN PATENT DOCUMENTS

| | | |
|---|---|---|
| 864810 | 7/1978 | Belgium . |
| 864819 | 7/1978 | Belgium . |
| 0007470 | 2/1980 | European Pat. Off. . |
| 0025017 | 3/1981 | European Pat. Off. . |
| 0027599 | 4/1981 | European Pat. Off. . |
| 2810922 | 7/1975 | Fed. Rep. of Germany . |
| 2137899 | 5/1972 | France . |
| 2387235 | 12/1975 | France . |
| 2384780 | 10/1977 | France . |
| 1399086 | 6/1975 | United Kingdom . |

*Primary Examiner*—Nicholas S. Rizzo
*Attorney, Agent, or Firm*—Oblon, Fisher, Spivak, McClelland & Maier

[57] ABSTRACT

The invention relates to cephem compounds of high antimicrobial activity, of the formula:

$$R^1 \underset{S}{\overset{N}{\rightthreetimes}} \underset{N}{\overset{C-CONH}{\underset{\|}{\rightthreetimes}}} \underset{O-R^2}{\rightthreetimes} \underset{O}{\rightthreetimes} \underset{N}{\overset{S}{\rightthreetimes}} \underset{COO^\ominus}{\overset{CH_2-\overset{\oplus}{N}}{\rightthreetimes}} \underset{R^4}{\overset{R^3}{\rightthreetimes}}$$

wherein
$R^1$ is amino or a protected amino group;
$R^2$ is lower alkyl which may be substituted with one carboxy, lower alkenyl, lower alkynyl, cyclo (lower) alkyl or cyclo (lower) alkenyl;
$R^3$ is lower alkylamino, N-(lower) alkanoyl (lower) alkylamino, di (lower) alkylamino, sulfo (lower) alkylamino, hydroxy (lower) alkylamino, N-(lower) alkanoylhydroxy (lower) alkylamino, alkanoyloxy (lower) alkyl, alkenoyloxy (lower) alkyl, lower alkoxy (lower) alkoxy (lower) alkyl, di (lower) alkylamino (lower) alkyl, lower alkylthio (lower) alkyl, lower alkylthio, lower alkoxy, lower alkoxy (lower) alkoxy, hydroxy (lower) alkoxy, lower alkanesulfonyl (lower) alkyl, hydroxy (lower) alkylthio, di (lower) alkylamino (lower) alkylthio, tetrazolyl, tetrazolylthio, tetrazolylthio (lower) alkyl or dihydrotriazinylthio (lower) alkyl substituted with oxo, hydroxy and lower alkyl; and
$R^4$ is hydrogen or lower alkyl; and pharmaceutically acceptable salts thereof.

16 Claims, No Drawings

CEPHEM COMPOUNDS

The present invention relates to new cephem compounds and pharmaceutically acceptable salts thereof. More particularly, it relates to new cephem compounds and pharmaceutically acceptable salts thereof, which have antimicrobial activities and to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I).

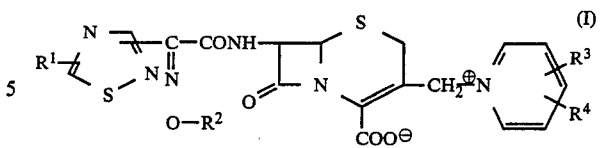

wherein
$R^1$ is amino or a protected amino group;

$R^2$ is lower aliphatic hydrocarbon group which may be substituted with suitable substituent(s), cyclo(lower)alkyl or cyclo(lower)alkenyl;

$R^3$ is lower alkylamino, N-protected (lower)alkylamino, di(lower)alkylamino, sulfo(lower)alkylamino, hydroxy(lower)-alkylamino, N-protected hydroxy(lower)-alkylamino, acyloxy(lower)alkyl, lower alkoxy(lower)alkoxy(lower)alkyl, di(lower)alkylamino(lower)alkyl, lower alkylthio(lower)alkyl, lower alkylthio, lower alkoxy, lower alkoxy-(lower)alkoxy, hydroxy(lower)alkoxy, acyl(lower)alkyl, hydroxy(lower)alkylthio, di(lower)alkylamino(lower)alkylthio, N-containing unsaturated 5-membered heterocyclic group, N-containing unsaturated 5-membered heterocyclicthio, or N-containing unsaturated 5 or 6-membered heterocyclicthio(lower)alkyl which may be substituted with suitable substituent(s); and $R^4$ is hydrogen or lower alkyl. According to the present invention, the new cephem compounds (I) can be prepared by various processes which are illustrated in the following scheme.

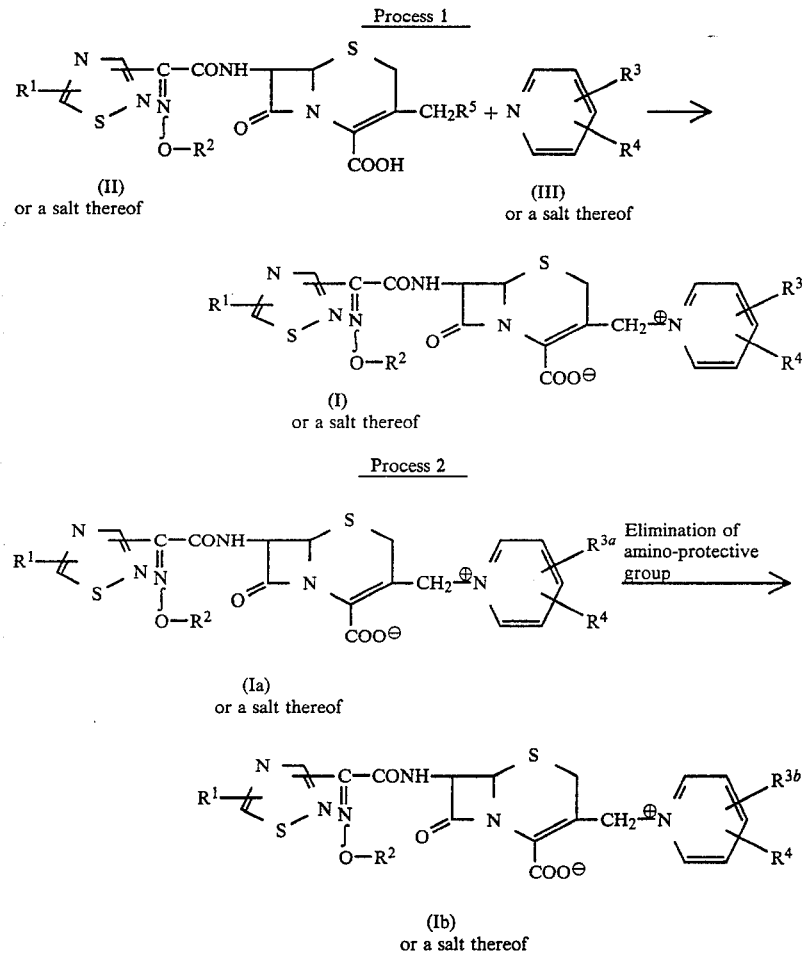

Process 3

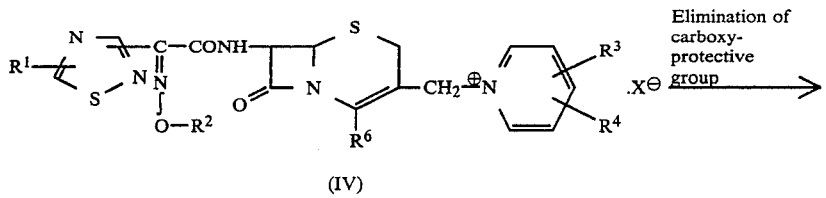

(IV)

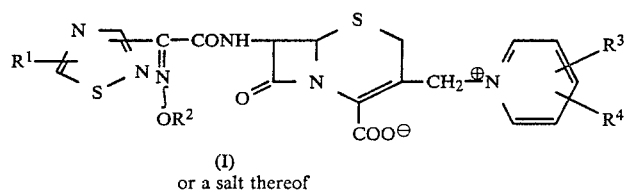

(I)
or a salt thereof wherein
R¹, R², R³ and R⁴ are each as defined above;
R⁵ is a group which can be substituted with a group of the formula:

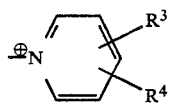

wherein R³ and R⁴ are each as defined above; $R^{3a}$ is N-protected (lower)alkylamino or N-protected hydroxy(lower)alkylamino; $R^{3b}$ is lower alkylamino or hydroxy-(lower)alkylamino;
R⁶ is a protected carboxy group; and
X is an acid residue.

Among the starting compounds of the present invention, the compound (IV) is novel and can be prepared by the following methods.

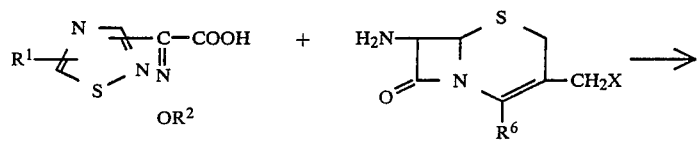

(V)
or its reactive derivative at the carboxy group or a salt thereof (VI)
or its reactive derivative at the amino group or a salt thereof

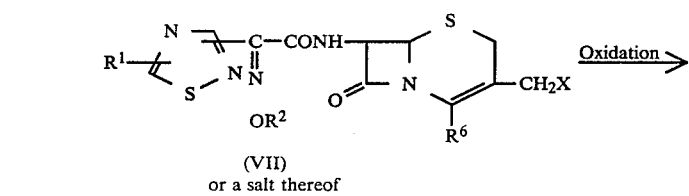

(VII)
or a salt thereof

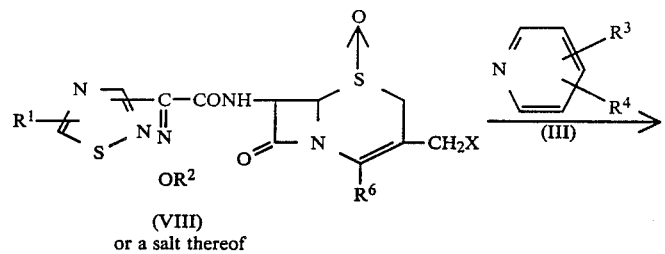

(VIII)
or a salt thereof

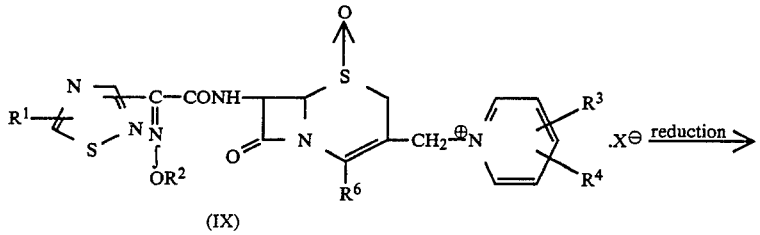

(IX)

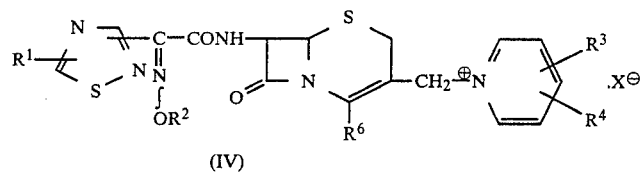

(IV)

wherein $R^1$, $R^2$, $R^3$, $R^4$, $R^6$ and X are each as defined above.

Some of the compound (V) can be prepared by the following methods.

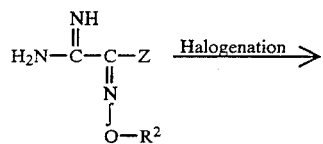

(X)
or a salt thereof

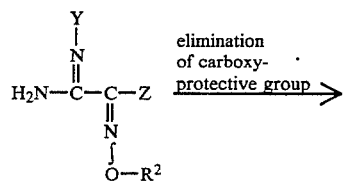

(XI)
or a salt thereof

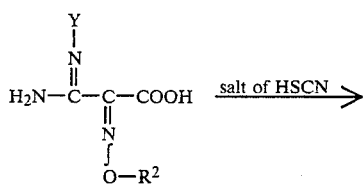

(XIII)
or a salt thereof

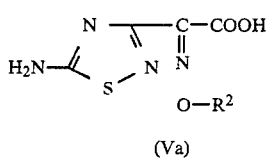

(Va)

wherein $R^2$ is as defined above, Z is protected carboxy group and Y is halogen.

Regarding the object compounds (I), (Ia) and (Ib) and the starting compounds (II), (IV), (V), (Va), (VII), (VIII), (IX), (X), (XI) and (XII), it is to be understood that said object and starting compounds include syn isomer, anti isomer and a mixture thereof. For example, with regard to the object compound (I), syn isomer means one geometrical isomer having the partial structure represented by the following formula:

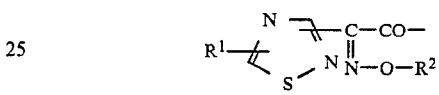

(wherein $R^1$ and $R^2$ are each as defined above) and anti isomer means the other geometrical isomer having the partial structure represented by the following formula:

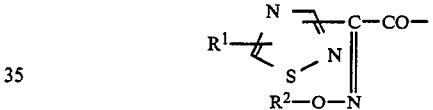

(wherein $R^1$ and $R^2$ are each as defined above).

Regarding the other object compounds and starting compounds as mentioned above, the syn isomer and the anti isomer can also be referred to the same geometrical isomers as illustrated for the compound (I).

Suitable pharmaceutically acceptable salts of the object compounds (I) are conventional non-toxic salt and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, etc.), an inorganic acid salt (e.g. hydrochloride, hydrobromide, hydroiodide, sulfate, phosphate, etc.), or a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable "protected amino" for $R^1$ may include an acylamino or an amino group substituted by a conventional protecting group such as ar(lower)alkyl which may have at least one suitable substituent(s), (e.g. benzyl, trityl, etc.) or the like.

Suitable protective groups in the terms "N-protected (lower)alkylamino" and "N-protected hydroxy(lower)alkylamino" may include acyl group and a conventional protective group such as aforesaid ar(lower)alkyl or the like.

Suitable acyl group and acyl moiety in the terms "acylamino", "acyloxy", "acyloxy(lower)alkyl" and "acyl(lower)alkyl" may include carbamoyl, aliphatic acyl group and acyl group containing an aromatic or heterocyclic ring. And, suitable examples of the said acyl may be carbamoyl, alkanoyl having 1 to 18 carbon atom(s) (e.g. formyl, acetyl, propionyl, butyryl, isobutyryl, valeryl, isovaleryl, oxalyl, succinyl, pivaloyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, etc.); alkenoyl having 3 to 20 carbon atoms (e.g., acryloyl, methacryloyl, crotonoyl, isocrotonoyl, pentenoyl, hexenoyl, heptenoyl, dodecenoyl, tetradecenoyl, hexadecenoyl, oleoyl, elaidoyl, etc.); lower alkoxycarbonyl having 2 to 7 carbon atoms (e.g. methoxycarbonyl, ethoxycarbonyl, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.); arenesulfonyl (e.g. benzenesulfonyl, tosyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc.), and the like. The acyl moiety as stated above may have at least one suitable substituent(s) such as halogen (chlorine, bromine, fluorine and iodine), lower alkanoyl or the like.

Suitable lower aliphatic hydrocarbon group may include lower alkyl, lower alkenyl, lower alkynyl and the like.

Suitable "lower alkyl" and "lower alkyl" moiety in the terms "lower alkylamino", "N-protected (lower)alkylamino", "di(lower)alkylamino", "sulfo(lower)alkylamino", "hydroxy(lower)alkylamino", "N-protected hydroxy(lower)-alkylamino", "hydroxy(lower)alkylthio", "di(lower)alkylamino(lower)alkylthio", "acyloxy(lower)alkyl", "lower alkoxy(lower)alkoxy(lower)alkyl", "di(lower)alkylamino(lower)alkyl", "lower alkylthio(lower)alkyl", "lower alkylthio", "acyl(lower)alkyl" and "N-containing unsaturated 5 or 6-membered heterocyclicthio(lower)alkyl" is one having 1 to 6 carbon atom(s) and may include methyl, ethyl, propyl, isopropyl, butyl, isobutyl, tert-butyl, pentyl, tertpentyl, hexyl and the like, and preferably one having 1 to 4 carbon atom(s).

Suitable "lower alkenyl" is one having 2 to 6 carbon atoms and may include vinyl, allyl, isopropenyl, 1-propenyl, 2-butenyl, 3-pentenyl and the like, and preferably one having 2 to 4 carbon atoms.

Suitable "lower alkynyl" is one having 2 to 6 carbon atoms and may include ethynyl, 2-propynyl, 2-butynyl, 3-pentynyl, 3-hexynyl and the like, and preferably one having 2 to 4 carbon atoms.

The lower aliphatic hydrocarbon group as mentioned above may be substituted with 1 to 3 suitable substituent(s) such as carboxy, protected carboxy as below, or the like.

Suitable "cyclo(lower)alkyl" is one having 3 to 6 carbon atoms and may include cyclopropyl, cyclobutyl, cyclopentyl, cyclohexyl and the like, and preferably one having 5 to 6 carbon atoms.

Suitable "cyclo(lower)alkenyl" is one having 3 to 6 carbon atoms and may include cyclopropenyl, cyclobutenyl, cyclopentenyl, cyclohexenyl and the like, and preferably one having 5 to 6 carbon atoms.

Suitable "lower alkoxy" and "lower alkoxy" moiety in the terms "lower alkoxy(lower)alkoxy(lower)alkyl", "lower alkoxy(lower)alkoxy" and "hydroxy(lower)alkoxy" may include methoxy, ethoxy, propoxy, isopropoxy, butoxy, t-butoxy, pentyloxy, hexyloxy and the like, and preferably one having 1 to 3 carbon atom(s).

Suitable "N-containing unsaturated 5-membered heterocyclic group" and "N-containing unsaturated 5-membered heterocyclic" moiety in the term "N-containing unsaturated 5-membered heterocyclicthio" may be unsaturated 5-membered heterocyclic group containing 1 to 4 nitrogen atom(s), for example, pyrrolyl, imidazolyl, pyrazolyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), or the like.

Suitable "N-containing unsaturated 5 or 6-membered heterocyclic" moiety in the term "N-containing unsaturated 5 or 6-membered heterocyclicthio(lower)alkyl which may be substituted with suitable substituent(s)" may be "N-containing unsaturated 5-membered heterocyclic group" as mentioned above and 1 to 4 N-containing unsaturated 6-membered heterocyclic group such as pyridyl, pyrimidinyl, pyrazinyl, pyridazinyl, triazinyl, dihydrotriazinyl or the like.

Said "N-containing unsaturated 5 or 6-membered heterocyclicthio(lower)alkyl" may be substituted with 1 to 3 suitable substituent(s) such as lower alkyl, hydroxy, oxo or the like.

Suitable $R^5$ may include an acid residue such as acyloxy, azido, halogen (e.g., chlorine, bromine, iodine or fluorine) or the like, wherein acyl moiety in the term "acyloxy" can be referred to the ones as exemplified above.

Suitable X may include acid residue as above.

Suitable "halogen" may be chlorine, bromine, fluorine or iodine.

Suitable "protected carboxy" may include esterified carboxy in which said ester may be the ones such as alkyl ester (e.g. methyl ester, ethyl ester, propyl ester, isopropyl ester, butyl ester, isobutyl ester, t-butyl ester, pentyl ester, t-pentyl ester, hexyl ester, heptyl ester, octyl ester, nonyl ester, decyl ester, undecyl ester, dodecyl ester, hexadecyl ester, etc.);

lower alkenyl ester (e.g. vinyl ester, allyl ester, etc.); lower alkynyl ester (e.g. ethynyl ester, propynyl ester, etc.); mono(or di or tri)-halo(lower)alkyl ester (e.g., 2-iodoethyl ester, 2,2,2-trichloroethyl ester, etc.); lower alkanoyloxy(lower)alkyl ester (e.g. acetoxymethyl ester, propionyloxymethyl ester, 1-acetoxypropyl ester, valeryloxymethyl ester, pivaloyloxymethyl ester, hexanoyloxymethyl ester, 1-acetoxyethyl ester, 2-propionyloxyethyl ester, 1-isobutyryloxyethyl ester, etc.); lower alkanesulfonyl(lower)alkyl ester (e.g., mesylmethyl ester, 2-mesylethyl ester, etc.); ar(lower)alkyl ester, for example, phenyl(lower)alkyl ester which may be substituted with one or more suitable substituent(s) (e.g. benzyl ester, 4-methoxybenzyl ester, 4-nitrobenzyl ester, phenethyl ester, trityl ester, diphenylmethyl ester, bis(methoxyphenyl)-methyl ester, 3,4-dimethoxybenzyl ester, 4-hydroxy-3,5-ditertiarybutylbenzyl ester, etc.); lower alkoxycarbonyloxy(lower)alkyl ester (e.g. methoxycarbonyloxymethyl ester, ethoxycarbonyloxymethyl ester, ethoxycarbonyloxyethyl ester, etc.) which may be substituted with azido; a heterocyclic ester, preferably benzotetrahydrofuryl ester which may be substituted with oxo group, more preferably phthalidyl ester; aroyloxy(lower)alkyl ester (e.g. benzoyloxymethyl ester, benzoyloxyethyl ester, toluoyloxyethyl ester, etc.); aryl ester which may have one or more suitable substituent(s) (e.g. phenyl ester, tolyl ester, tertiarybutylphenyl ester, xylyl ester, mesityl ester, cumenyl ester, etc.), and the like. Preferable example of "protected carboxy" may be lower alkoxycarbonyl (e.g. methoxycarbonyl, ethoxycarbonyl, propoxycarbonyl, butoxycarbonyl, t-butoxycarbonyl, etc.) or ar(-lower)alkoxycarbonyl (e.g. benzyloxycarbonyl, phenethyloxycarbonyl, trityloxycarbonyl, diphenylmethoxycarbonyl, etc.).

Preferred embodiments of the object compound (I) are as follows.

Preferred embodiment of $R^1$ is amino; $R^2$ is lower alkyl, carboxy(lower)alkyl, lower alkynyl, cyclo(lower)alkyl, cyclo(lower)alkenyl or lower alkenyl; $R^3$ is lower alkylamino, N-acyl(lower)alkylamino [more preferably N-(lower)alkanoyl(lower)alkylamino], di(-lower)alkylamino, sulfo(lower)alkylamino, hydroxy(-lower)alkylamino, N-acyl hydroxy(lower)-alkylamino [more preferably N-(lower)alkanoyl hydroxy(lower)alkylamino], acyloxy(lower)alkyl [more preferably alkanoyloxy(lower)alkyl or alkenoyloxy(lower)alkyl], hydroxy(lower)alkoxy, lower alkoxy(lower)alkoxy(-lower)alkyl, di(lower)-alkylamino(lower)alkyl, hydroxy(lower)alkylthio, lower alkylthio(lower)alkyl, lower alkylthio, lower alkoxy(lower)alkoxy, di(lower)alkylamino(lower)alkylthio, lower alkoxy, acyl(lower)alkyl [more preferably lower alkanesulfonyl(lower)alkyl], N-containing unsaturated 5-membered heterocyclic group [more preferably tetrazolyl], N-containing unsaturated 5-membered heterocyclicthio [more preferably tetrazolylthio] or N-containing unsaturated 5 or 6-membered heterocyclicthio(lower)alkyl [more preferably tetrazolylthio(lower)alkyl or dihydrotriazinylthio(lower)alkyl] which may be substituted with lower alkyl, hydroxy and/or oxo; and $R^4$ is hydrogen or lower alkyl.

The processes for preparing the object compounds of the present invention are explained in details in the following.

PROCESS 1

The object compound (I) or a salt thereof can be prepared by reacting the compound (II) or a salt thereof with the compound (III) or a salt thereof.

Suitable salt of the compounds (II) and (III) can be referred to the ones exemplified for the compound (I).

The present reaction may be carried out in a solvent such as water, phosphate buffer, phosphoric acid, acetone, chloroform, acetonitrile, nitrobenzene, methylene chloride, ethylene chloride, formamide, dimethylformamide, methanol, ethanol, ether, tetrahydrofuran, dimethylsulfoxide, or any other organic solvent which does not adversely affect the reaction, preferably in ones having strong polarities. Among the solvents, hydrophilic solvents may be used in a mixture with water. The reaction is preferably carried out in around neutral medium. When the compound (II) is used in a free form, the reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out at ambient temperature, under warming or under heating. The present reaction is preferably carried out in the presence of alkali metal halide (e.g. sodium iodide, potassium iodide, etc.), alkali metal thiocyanate (e.g. sodium thiocyanate, potassium thiocyanate, etc.) etc.

PROCESS 2

The object compound (Ib) or a salt thereof can be prepared by subjecting the compound (Ia) or a salt thereof to elimination reaction of the protective group of amino.

Suitable salts of the compounds (Ia) and (Ib) can be referred to the ones exemplified for the compound (I).

The present elimination reaction is carried out in accordance with a conventional method such as hydrolysis; reduction; a method by reacting the compound (Ia) wherein the protective group is acyl group with iminohalogenating agent and then with iminoetherifying agent, and, if necessary, subjecting the resulting compound to hydrolysis; or the like. The hydrolysis may include a method using an acid or base or hydrazine and the like. These methods may be selected depending on the kind of the protective groups to be eliminated.

Among these methods, hydrolysis using an acid is one of the common and preferable method for eliminating the protective group such as substituted or unsubstituted alkoxycarbonyl (e.g. t-pentyloxycarbonyl, t-butoxycarbonyl, etc.), alkanoyl (e.g. formyl, etc.), cycloalkoxycarbonyl, substituted or unsubstituted aralkoxycarbonyl (e.g. benzyloxycarbonyl, substituted benzyloxycarbonyl, etc.), ar(lower)alkyl (e.g. benzyl, trityl, etc.) or the like.

Suitable acid may include an organic or an inorganic acid, for example, formic acid, trifluoroacetic acid, benzenesulfonic acid, p-toluenesulfonic acid, hydrochloric acid and the like, and preferable acid is, for example, formic acid, trifluoroacetic acid, hydrochloric acid, etc. The acid suitable for the reaction can be selected according to the kind of protective group to be eliminated. When the elimination reaction is conducted with the acid, it can be carried out in the presence or absence of a solvent. Suitable solvent may include a conventional organic solvent, water or a mixture thereof. When trifluoroacetic acid is used, the elimination reaction may preferably be carried out in the presence of anisole.

The hydrolysis using hydrazine is commonly applied for eliminating the protective group, for example, succinyl or phthaloyl.

The hydrolysis with a base is preferably applied for eliminating acyl group, for example, haloalkanoyl (e.g. dichloroacetyl, trifluoroacetyl, etc.) etc. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-ene, 1,4-diazabicyclo[2,2,2]octane 1,5-diazabicyclo[5,4,0]undecene-5 or the like. The hydrolysis using a base is often carried out in water, a conventional organic solvent or a mixture thereof.

Among the protective group, the acyl group can be generally eliminated by hydrolysis as mentioned above or by the other conventional hydrolysis. In case that the acyl group is halogen substituted-alkoxycarbonyl or 8-quinolyloxycarbonyl, they are eliminated by treating with a heavy metal such as copper, zinc or the like.

The reductive elimination is generally applied for eliminating the protective group, for example, haloalkoxycarbonyl (e.g. trichloroethoxycarbonyl, etc.), substituted or unsubstituted aralkoxycarbonyl (e.g. benzyloxycarbonyl, substituted benzyloxycarbonyl etc.), 2-pyridylmethoxycarbonyl, etc. Suitable reduction may include, for example, reduction with an alkali metal borohydride (e.g. sodium borohydride, etc.) and the like.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

The present reaction includes, within its scope, the cases that the protected amino group for $R^1$ is transformed into the free amino group in the course of the elimination reaction as mentioned above or in the post-treatment of the reaction mixture of reaction product.

PROCESS 3

The compound (I) or a salt thereof can be prepared by subjecting the compound (IV) to elimination reaction of carboxy-protective group.

The present reaction is carried out in accordance with a conventional method such as hydrolysis, reduction or the like.

In case that the protective group is an ester, the protective group can be eliminated by hydrolysis. Hydrolysis is preferably carried out in the presence of a base or an acid. Suitable base may include an inorganic base and an organic base such as an alkali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), picoline, 1,5-diazabicyclo[4,3,0]-none-5-ene, 1,4-diazabicyclo[2,2,2]octane, 1,8-diazabicyclo-[5,4,0]undecene-7, or the like. Suitable acid may include an organic acid (e.g. formic acid, acetic acid, propionic acid, trifluoroacetic acid, etc.) and an inorganic acid (e.g. hydrochloric acid, hydrobromic acid, sulfuric acid, etc.).

In case that trifluoroacetic acid is used, the reaction is preferably carried out in the presence of anisole.

The reaction is usually carried out in a solvent such as water, an alcohol (e.g. methanol, ethanol, etc.), a mixture thereof or any other solvent which does not adversely influence to the reaction. A liquid base or acid can be also used as the solvent. The reaction temperature is not critical and the reaction is usually carried out under cooling to warming.

Reduction can be applied preferably for elimination of the protective group such as 4-nitrobenzyl, 2-iodoethyl, 2,2,2-trichloroethyl, or the like. The reduction method applicable for the elimination reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst (e.g. palladiumcarbon, etc.).

The preparations of the starting compound (IV) are explained in detail in the following.

PREPARATION 1

The compound (VII) can be prepared by reacting the compound (V) or its reactive derivative at the carboxy group or a salt thereof with the compound (VI) or its reactive derivative at the amino group or a salt thereof.

The present reaction can be carried out in a conventional manner used in an acylation reaction at 7-amino position of cephalosporin compounds.

PREPARATION 2

The compound (VIII) or a salt thereof can be prepared by oxidizing the compound (VII) or a salt thereof.

Suitable oxidizing agent to be used in this reaction may include all oxidizing agent which can oxidize —S— group in cephalosporin compounds to

group, for example, peroxide (e.g., hydrogen peroxide, 3-chloroperbenzoic acid, etc.) and the like.

The reaction is usually carried out in solvent such as methylene chloride or any other solvent which does not adversely affect the reaction. The reaction temperature is not critical and preferably under cooling or at ambient temperature.

PREPARATION 3

The compound (IX) can be prepared by reacting the compound (VIII) or a salt thereof with the compound (III).

The reaction can be carried out according to a similar manner to that of Process 1.

PREPARATION 4

The compound (IV) can be prepared by reducing the compound (IX).

The present reduction can be carried out in the presence of conventional reducing agent which can reduce

group in cephalosporin compound to —S— group, for example, phosphorus halide such as phosphorus trihalide (e.g., phosphorus trichloride, etc.).

The preparations of the compound (Va) are explained in detail in the following.

PREPARATION 5

The compound (XI) or a salt thereof can be prepared by subjecting the compound (X) or a salt thereof to halogenation.

Suitable salt of the compound (X) and (XI) can be referred to acid addition salt as exemplified for the compound (I).

The present reaction can be carried out by reacting the compound (X) or a salt thereof with halogenating agent.

Suitable halogenating agent used in the present reaction may include halogen (e.g., chlorine, bromine, fluorine or iodine), N-halogenosuccinimide (e.g., N-chlorosuccinimide, N-bromosuccinimide, etc.), hypohalogenous acid (e.g., hyprochlorous acid, hypobromous acid, etc.), isocyanuric acid halide (e.g., isocyanuric acid chloride, isocyanuric acid bromide, etc.) and the like.

The reaction is usually carried out in a solvent which does not adversely affect the reaction such as ether, alcohol (e.g., methanol, ethanol, etc.), mixture thereof or the like.

The reaction temperature is not critical and the reaction is usually carried out from under cooling to at ambient temperature.

PREPARATION 6

The compound (XII) or a salt thereof can be prepared by subjecting the compund (XI) or a salt thereof to elimination reaction of carboxy-protective group.

The present elimination reaction can be carried out according to a similar manner to that of Process 3.

PREPARATION 7

The compound (Va) or a salt thereof can be prepared by reacting the compound (XII) or a salt thereof with salt of thiocyanic acid (HSCN).

Suitable salt of the compound (XII) and (Va) can be referred to the ones as exemplified for the compound (I).

Suitable salt of thiocyanic acid may include metal salt such as alkali metal salt (e.g. sodium salt, potassium salt, etc.) or the like, salt with an organic tertiary base (e.g., trimethylamine, triethylamine, dimethylaniline, etc.) and the like.

The present reaction is usually carried out in a solvent which does not adversely affect the reaction, for example, hydrophilic solvent such as an alcohol (e.g., methanol, ethanol, etc.) or the like.

The reaction temperature is not critical and the reaction is usually carried out from under cooling to at ambient temperature.

The object compound (I) of the present invention exhibits high antimicrobial activity and inhibits the growth of a number of microorganisms including pathogenic Gram-positive and Gram-negative bacteria.

For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives.

While the dosage of the compounds may vary from and also depend upon the age and condition of the patient, an average single dose of about 50 mg., 100 mg., 250 mg., and 500 mg. of the compounds according to the present invention has proved to be effective for treating of infectious diseases caused by a number of pathogenic bacteria. In general amounts, daily dose between 1 mg/body and about 1000 mg/body or even more may be administered.

Now in order to show the utility of the object compound (I), test data on anti-microbial activity of representative compounds of the present invention are shown below.

TEST METHOD

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of μg/ml after incubation at 37° C. for 20 hours.

TEST COMPOUND (1) 7-[2-Ethoxyimino-2-(5-amino-1,2,4,-thiadiazol-3-yl)acetamido]-3-(3-methylamino-1-pyridiniomethyl)-3-cephem-4-carboxylate (syn isomer)

(2) 7-[2-Ethoxyimino-2-(5-amino-1,2,4-thiadiazol-3-yl)acetamido]-3-(3-dimethylamino-1-pyridiniomethyl)-3-cephem-4-carboxylate (syn isomer).

(3) 7-[2-Ethoxyimino-2-(5-amino-1,2,4-thiadiazol-3-yl)acetamido]-3-(3-methoxy-1-pyridiniomethyl)-3-cephem-4-carboxylate (syn isomer).

TEST RESULTS

| | MIC (μg/ml) | | |
|---|---|---|---|
| | Test Compound | | |
| Test Bacteria | (1) | (2) | (3) |
| B. subtilis ATCC 6633 | 0.78 | 0.39 | 0.78 |
| S. marcescens 35 | 1.56 | 1.56 | 1.56 |

The following Preparations and Examples are given for the purpose of illustrating the present invention.

PREPARATION 1

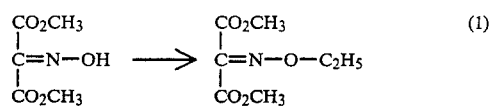

(1)

To a mixture of dimethyl isonitrosomalonate (12.25 g) and diethyl sulfate (14.32 g) in N,N-dimethylformamide (12 ml) was dropped triethylamine (9.39 g) at 30° to 40° C. under stirring, which was continued for 1.5 hours at the same temperature. The mixture was diluted with methylene chloride (45 ml) and water (30 ml), and then the organic layer was separated out, washed with 5% aqueous potassium carbonate and water, dried over magnesium sulfate and evaporated to give an oily residue (11.5 g). The residue was distilled under reduced pressure (5 mmHg) to give dimethyl ethoxyiminomalonate (5.5 g), bp. 85° to 105° C. (5 mmHg).

IR (Film): 3000, 2970, 1755, 1730, 1610 cm$^{-1}$.

NMR (CDCl$_3$, δ): 1.30 (3H, t, J=7 Hz), 3.83 (6H, s), 4.32 (2H, q, J=7 Hz).

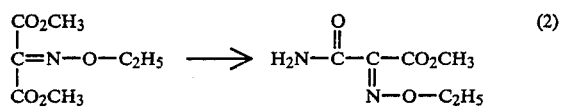

A mixture of dimethyl ethoxyiminomalonate (57.4 g) and conc. ammonium hydroxide (50 ml) in methanol (150 ml) was stirred for 2.5 hours at room temperature. The mixture was adjusted to pH 4 with conc. hydrochloric acid under cooling and concentrated to 70 ml under reduced pressure. The aqueous solution was stood in a refrigerator for one hour and the resulting precipitates were collected by filtration, washed with cold water and dried to give methyl 2-carbamoyl-2-ethoxyiminoacetate (syn isomer) (31 g), mp 68° to 71° C.

IR (Nujol): 3450, 3300, 3200, 1740, 1680, 1660, 1600 cm$^{-1}$.

NMR (DMSO-d$_6$, δ): 1.28 (3H, t, J=7 Hz), 3.83 (3H, s), 4.28 (2H, q, J=7 Hz), 7.70 (2H, broad s).

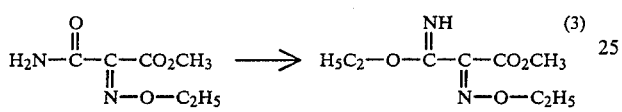

To a solution of Meerwein reagent (triethyloxonium tetrafluoroborate) {prepared from boron fluoride etherate (2.84 g) by a method of Org. Syn., 46, 113 (1966)} in methylene chloride (30 ml) was added methyl 2-carbamoyl-2-ethoxyiminoacetate (syn isomer, 2.6 g) and the mixture was stirred for 18 hours at room temperature. The reaction mixture was cooled in an ice-bath and triethylamine (3 g) was added thereto, followed by an addition of water (20 ml). The organic layer was separated out, dried over magnesium sulfate and evaporated to give crude methyl 3-imino-3-ethoxy-2-ethoxyiminopropionate (syn isomer) (5.0 g) as an oil.

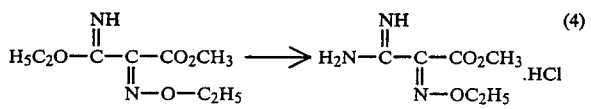

A solution of the above obtained crude methyl 3-imino-3-ethoxy-2-ethoxyiminopropionate (syn isomer) (5.0 g) and ammonium chloride (802 mg) in methanol (25 ml) was stirred for 6 hours at room temperature and evaporated to dryness to give a residue.

The residue was triturated with ethyl acetate to give methyl 2-amidino-2-ethoxyiminoacetate hydrochloride (syn isomer) (1.75 g), mp. 138° to 140° C. (dec.).

IR (Nujol): 2600, 2490, 1740, 1680, 1595 cm$^{-1}$.

NMR (DMSO-d$_6$, δ): 1.33 (3H, t, J=7 Hz), 3.90 (3H, s), 4.45 (2H, q, J=7 Hz).

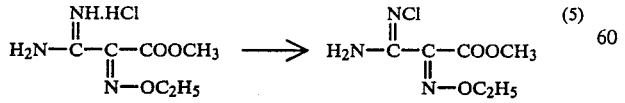

To a solution of methyl 2-amidino-2-ethoxyiminoacetate hydrochloride (syn isomer) (12.6 g) in methanol (300 ml) was dropped an ethereal solution (90 ml) of hypochlorous acid [prepared from 10% aqueous solution (100 ml) of sodium hypochlorite and 3N hydrochloric acid (60 ml) in diethyl ether (100 ml)] at 0° to 5° C. under cooling in an ice bath and stirring, which was continued for 30 minutes at the same temperature. To the reaction mixture was dropped triethylamine (14 g) at the same temperature and they were evaporated to dryness. The residue was triturated in cold water (150 ml) and stirred for 30 minutes in an ice bath. The resulting precipitates were collected by filtration, washed with cold water and dried to give methyl 2-(N$^2$-chloro)amidino-2-ethoxyiminoacetate (syn isomer) (7.2 g), mp 38° to 40° C.

IR (Nujol): 3470, 3350, 1750, 1635, 1600, 1560, 1030, 840 cm$^{-1}$.

NMR (CD$_3$OD, δ): 1.23 (3H, t, J=7 Hz), 3.76 (3H, s), 4.20 (2H, q, J=7 Hz).

(6) A suspended solution of methyl 2-(N$^2$-chloro)amidino-2-ethoxyiminoacetate (syn isomer) (6.0 g) in 1N aqueous solution of sodium hydroxide (30 ml) was stirred for one hour at room temperature. The solution was cooled in an ice bath, acidified with 6N hydrochloric acid (5.5 ml) and extracted with ethyl acetate (30 ml×2). The extract was dried over, evaporated and the residue was triturated in a mixed solvent of diisopropyl ether and petroleum ether to give 2-(N$^2$-chloro)amidino-2-ethoxyiminoacetic acid (syn isomer) (5.0 g), mp 125° to 126° C. (dec.).

IR (Nujol): 3480, 3370, 2800-2200, 1740, 1620, 1600, 1380, 1040, 970, 820 cm$^{-1}$.

NMR (CD$_3$OD, δ): 1.30 (3H, t, J=7 Hz), 4.25 (2H, q, J=7 Hz).

(7) To a solution of potassium thiocyanate (970 mg) and triethylamine (1.2 g) in methanol (40 ml) was added 2-(N$^2$-chloro)amidino-2-ethoxyiminoacetic acid (syn isomer) (2.13 g) at −5° to 0° C. under cooling in an ice-salt bath and stirring. The mixture was stirred for 30 minutes at the same temperature and allowed to stand overnight in a refrigerator. The mixture was evaporated to dryness, the residue was dissolved in water (10 ml), adjusted to pH 1.5 with 3N hydrochloric acid and extracted with ethyl acetate. The extract was dried over magnesium sulfate, evaporated to dryness and triturated in diisopropyl ether to give 2-ethoxyimino-2-(5-amino-1,2,4-thiadiazol-3-yl)-acetic acid (syn isomer) (1.67 g), mp 164° to 165° C. (dec.).

PREPARATION 2

To a solution of phosphorus pentachloride (54.6 g) in methylene chloride (500 ml) was added 2-ethoxyimino-2-(5-amino-1,2,4-thiadiazol-3-yl)-acetic acid (syn isomer) (54.0 g) under stirring and cooling at −20° C. The mixture was stirred for 30 minutes at −15° to −12° C. and for 2 hours at −5° C. To the mixture containing precipitates of an object compound was added diisopropyl ether (500 ml) at −5° C. and the mixture was stirred for 30 minutes at −5° to 10° C. The resulting precipitates were collected by filtration, washed with diisopropyl ether and dried to give 2-ethoxyimino-2-(5-amino-1,2,4-thiadiazol-3-yl)acetyl chloride hydrochloride (syn isomer) (60.17 g), mp. 125° to 127° C. (dec.).

I.R. (Nujol): 1785, 1625, 1055 cm$^{-1}$ Analysis for C$_6$H$_8$O$_2$N$_4$SCl$_2$.

| | C | H | N | S | Cl |
|---|---|---|---|---|---|
| calc'd: | 26.57 | 2.95 | 20.66 | 11.81 | 26.20 |
| found: | 26.13 | 2.99 | 20.49 | 11.77 | 26.41 |

PREPARATION 3

To a suspension of diphenylmethyl 7-amino-3-chloromethyl-3-cephem-4-carboxylate hydrochloride (27 g) in methylene chloride (300 ml) was added N,N-dimethylaniline (36.2 g) under cooling in an ice bath at 5° C. To the solution was added portionwise 2-ethoxyimino-2-(5-amino-1,2,4-thiadiazol-3-yl)acetyl chloride hydrochloride (syn isomer) (16.2 g) below 11° C. and the mixture was stirred for 45 minutes at 5° C. The reaction mixture was diluted with a mixed solvent of methylene chloride (100 ml) and water (200 ml) and adjusted to pH 2 with 1N hydrochloric acid. The organic layer was separated out, washed with water, dried over magnesium sulfate and evaporated to dryness. The residue was triturated in diethyl ether to give diphenylmethyl 7-[2-ethoxyimino-2-(5-amino-1,2,4-thiadiazol-3-yl)acetamido]-3-chloromethyl-3-cephem-4-carboxylate (syn isomer) (32.4 g), mp 120° to 125° C. (dec.).

IR (Nujol): 3300, 3150, 1780, 1725, 1675, 1625, 1530, 1495 $cm^{-1}$.

NMR (DMSO-$d_6$, $\delta$): 1.28 (3H, t, J=7 Hz), 3.68 (2H, broad s), 4.23 (2H, q, J=7 Hz), 4.47 (2H, s), 5.27 (1H, d, J=5 Hz), 5.97 (1H, 2d, J=5 and 8 Hz), 7.0 (1H, s), 7.2–7.7 (10H, m), 8.17 (2H, broad s), 9.62 (1H, d, J=8 Hz).

PREPARATION 4

To a cold solution of diphenylmethyl 7-[2-ethoxyimino-2-(5-amino-1,2,4-thiadiazol-3-yl)acetamido]-3-chloromethyl-3-cephem-4-carboxylate (syn isomer) (10 g) in a mixed solution of methylene chloride (100 ml) and acetic acid (10 ml) were added 30% hydrogen peroxide (1.84 ml) and sodium tungstate (0.3 g).

The mixture was stirred for 45 minutes in an ice bath and poured into diethyl ether (300 ml). The precipitates were collected by filtration and washed with diethyl ether to give diphenylmethyl 7-[2-ethoxyimino-2-(5-amino-1,2,4-thiadiazol-3-yl)-acetamido]-3-chloromethyl-3-cephem-4-carboxylate-1-oxide (syn isomer) (8.9 g), mp 150° to 155° C. (dec.).

IR (Nujol): 3280, 3170, 1785, 1723, 1667, 1628, 1530 $cm^{-1}$.

NMR (DMSO-$d_6$, $\delta$): 1.30 (3H, t, J=7 Hz), 3.90 (2H, broad s), 4.23 (2H, q, J=7 Hz), 4.58 (2H, broad s), 5.12 (1H, d, J=5 Hz), 6.10 (1H, 2d, J=5 and 8 Hz), 7.02 (1H, s), 7.20–7.73 (10H, m), 8.15 (2H, broad s), 9.00 (1H, d, J=8 Hz).

PREPARATION 5

A mixture of diphenylmethyl 7-[2-ethoxyimino-2-(5-amino-1,2,4-thiadiazol-3-yl)acetamido]-3-chloromethyl-3-cephem-4-carboxylate-1-oxide (syn isomer) (3 g) and 3-dimethylaminopyridine (0.7 g) in tetrahydrofuran (20 ml) was stirred for 2.5 hours at 48° to 50° C. The resulting precipitate was filtered, washed with tetrahydrofuran and dried to give diphenylmethyl 7-[2-ethoxyimino-2-(5-amino-1,2,4-thiadiazol-3-yl)acetamido]-3-(3-dimethylamino-1-pyridiniomethyl)-3-cephem-4-carboxylate-1-oxide chloride (syn isomer) (3.18 g), mp 120° to 130° C. (dec.).

IR (Nujol): 3250, 1800, 1720, 1670, 1620, 1580, 1525 $cm^{-1}$.

NMR (DMSO-$d_6$, $\delta$): 1.17 (3H, t, J=7 Hz), 3.00 (6H, s), 3.90 (2H, m), 4.18 (2H, q, J=7 Hz), 5.22 (1H, d, J=4 Hz), 5.50 (2H, m), 6.10 (1H, dd, J=4 and 8 Hz), 6.94 (1H, s), 7.35 (10H, m), 7.70 (2H, m), 8.03 (2H, m), 8.22 (2H, m), 9.03 (1H, d, J=8 Hz).

PREPARATION 6

To a mixture of diphenylmethyl 7-[2-ethoxyimino-2-(A5-amino-1,2,4-thiadiazol-3-yl)acetamido]-3-(3-dimethylamino-1-pyridiniomethyl)-3-cephem-4-carboxylate-1-oxide chloride (syn isomer) (3.12 g) and N,N-dimethylaniline (1.01 g) in acetonitrile (31 ml) was dropped phosphorus trichloride (1.14 g) under cooling in an ice-salt bath and stirring, which was continued for 1.5 hours at the same condition. To the reaction mixture was added diethyl ether (200 ml) and stirred for 30 minutes. A resulting precipitate was filtered, washed with diethyl ether and dried to give diphenylmethyl 7-[2-ethoxyimino-2-(5-amino-1,2,4-thiadiazol-3-yl)acetamido]-3-(3-dimethylamino-1-pyridiniomethyl)-3-cephem-4-carboxylate chloride (syn isomer) (2.96 g), mp 97° to 107° C. (dec.).

IR (Film): 1780, 1740, 1680, 1620, 1580, 1525 $cm^{-1}$.

NMR (DMSO-$d_6$+$D_2O$, $\delta$): 1.25 (3H, t, J=7 Hz), 3.10 (6H, s), 3.67 (2H, m), 4.19 (2H, q, J=7 Hz), 5.37 (1H, d, J=5 Hz), 5.5 (2H, m), 6.07 (1H, d, J=5 Hz), 7.00 (1H, s), 7.45 (10H, m), 7.67–8.15 (3H, m), 8.22 (1H, m).

PREPARATION 7

To a solution of 4-hydroxymethylpyridine (10.02 g) and triethylamine (9.27 g) in tetrahydrofuran (100 ml) was dropped a solution of hexadecanoyl chloride (25.2 g) in tetrahydrofuran (80 ml) under cooling in an ice bath and stirring, which was continued for one hour at the same temperature. A resulting precipitate was filtered off and the filtrate was evaporated to dryness. The residue was dissolved in diether ether, washed with water, dried over magnesium sulfate and evaporated. The residue was purified by column chromatography on silica gel (250 g) using methylene chloride-ethyl acetate as an eluent to give 4-hexadecanoyloxymethylpyridine (14.3 g).

NMR (CDCl$_3$, $\delta$): 0.88 (3H, m), 1.28 (26H, m), 2.39 (2H, t, J=7 Hz), 5.07 (2H, s), 7.15 (2H, m), 8.50 (2H, m).

PREPARATION 8

The following compounds were obtained according to a similar manner to that of Preparation 7.

(1) 4-Dodecanoyloxymethylpyridine (oil). IR (Film): 1745, 1610, 1570, 1465, 1420, 1380, 1360, 1240, 1160, 1115, 1075, 1050 $cm^{-1}$.

NMR (CCl$_4$, $\delta$): 0.88 (3H, m), 1.27 (18H, m), 2.33 (2H, t, J=6 Hz), 5.02 (2H, s), 7.10 (2H, m), 8.45 (2H, m).

(2) 4-(3-Hexadecanoyloxypropyl)pyridine, mp 37° to 40° C.

IR (Nujol): 1730, 1605, 1175 $cm^{-1}$.

(3) 4-Oleoyloxymethylpyridine, oil.

IR (Film): 3020, 2950, 2870, 1746, 1608 $cm^{-1}$.

PREPARATION 9

A mixture of 3-aminopyridine (2.82 g) and sodium hydroxymethanesulfonate monohydrate (9.12 g) in water (40 ml) was stirred for 1.5 hours at 80° C. The solution was concentrated to yield a precipitate and stood for several hours. The resulting precipitate was filtered, washed with ethanol and dried to give sodium 3-pyridylaminomethanesulfonate (3.71 g), mp 211° to 220° C.

IR (Nujol): 3600, 3530, 3250, 3200, 1640, 1590, 1490 $cm^{-1}$.

NMR DMSO-$d_6$, $\delta$): 4.05 (2H, d, J=6 Hz), 6.30 (1H, t, J=6 Hz), 7.05 (2H, m), 7.74 (1H, m), 8.10 (1H, m).

PREPARATION 10

A mixture of 3-bromopyridine (25.10 g), ethanolamine (34.89 g) and cupric sulfate (2.90 g) in water (140 ml) was refluxed for 5 hours under stirring. The reaction mixture was washed with chloroform and the aqueous layer was separated out. To the aqueous solution was added an aqueous solution of potassium carbonate (22 g) and then the mixture was saturated with sodium chloride, and extracted with a mixed solvent of chloroform and ethanol (1:1). The extract was evaporated and the residue was subjected to column chromatography on silica gel (200 g) using a mixed solvent of chloroform and ethanol (5:1) as an eluent. The fractions containing an object compound were collected and evaporated to give 3-(2-hydroxyethyl)aminopyridine (5.96 g) as an oil.

IR (Film): 3500–3050, 2950, 2850, 1590, 1515, 1490, 1460, 1420, 1380, 1330, 1305, 1250, 1190, 1140, 1070, 1050, 800, 710 cm$^{-1}$.

NMR (CCl$_4$+CDCl$_3$, δ): 3.13 (2H, t, J=5 Hz), 3.73 (2H, t, J=5 Hz), 4.89 (2H, broad s), 6.85 (2H, m), 7.77 (2H, m).

PREPARATION 11

A mixture of formic acid (5.02 g) and acetic anhydride (11.14 g) was stirred for 30 minutes at 40° to 45° C. and cooled in an ice bath. To the cold mixed anhydride was added a solution of 3-(2-hydroxyethyl)aminopyridine (5.80 g) in tetrahydrofuran (20 ml) under cooling in an ice bath and stirring, which was continued for two hours at room temperature. The mixture was evaporated to remove tetrahydrofuran and poured into water (100 ml). The mixture was adjusted to pH 6 to 7 with sodium bicarbonate and extracted with methylene chloride. The extract was washed with a saturated aqueous solution of sodium chloride, dried over magnesium sulfate and evaporated to give 3-[N-(2-formyloxyethyl)-formamido]-pyridine (7.47 g) as an oil.

IR (Film): 3075, 2975, 2910, 1725, 1700–1655, 1585, 1490, 1435, 1415, 1355, 1295, 1230, 1190–1160, 1110, 1030, 940, 815, 715 cm$^{-1}$.

NMR (CDCl$_3$, δ): 4.23 (4H, m), 7.50 (2H, m), 7.93 (1H, s), 8.35 (1H, s), 8.53 (2H, m).

PREPARATION 12

A mixture of 3-[N-(2-formyloxyethyl)formamido]-pyridine (7.01 g) and sodium bicarbonate (3.04 g) in a mixed solution of tetrahydrofuran (60 ml) and water (110 ml) was stirred for 8 hours at 45° to 46° C. The reaction mixture was extracted with a mixed solvent of chloroform and ethanol (1:1) and the extract was evaporated. The residue was dissolved in a mixed solvent of chloroform and ethanol (4:1) and subjected to column chromatography on silica gel (150 g). The elution was carried out with the same solvent and the fractions containing an object compound were collected and evaporated to give 3-[N-(2-hydroxyethyl)formamido]-pyridine (4.60 g) as an oil.

IR (Film): 3600–3050, 3000, 2950, 2900, 1700–1650, 1585, 1490, 1430, 1350, 1290, 1190, 1080–1050, 870, 810, 710 cm$^{-1}$.

NMR (CDCl$_3$, δ): 3.84 (5H, m), 7.50 (2H, m), 8.31 (1H, s), 8.45 (2H, m).

EXAMPLE 1

A mixture of 3-(N-methylformamido)pyridine (3.26 g), sodium iodide (21.58 g), phosphoric acid (0.71 g), water (3 ml) and acetonitrile (9 ml) was heated at 65° to 70° C. under stirring and sodium 7-[2-ethoxyimino-2-(5-amino-1,2,4-thiadiazol-3-yl)acetamido]cephalosporanate (syn isomer) (5.90 g) was added thereto. The mixture was stirred for 1.5 hours at 70° to 72° C. and diluted with water (30 ml). The aqueous solution was cooled, adjusted to pH 3 with 6N hydrochloric acid and diluted with water to 150 ml. The aqueous solution was washed five times with a mixed solvent (100 ml) of chloroform and ethanal (2:1) and concentrated to 200 ml under reduced pressure. An insoluble material was filtered off and the filtrate was subjected to column chromatography on a non ionic adsorption resin "Diaion HP 20" (Trademark: Prepared by Mitsubishi Chemical Industries) (200 ml). After the column was washed with water, the elution was carried out with 10% aqueous methanol. The eluates containing an object compound were collected, evaporated to remove methanol under reduced pressure and lyophilized to give 7-[2-ethoxyimino-2-(5-amino-1,2,4-thiadiazol-3-yl)acetamido]-3-[3-(N-methylformamido)-1-pyridiniomethyl]-3-cephem-4-carboxylate (syn isomer), (3.14 g), mp 120° to 127° C. (dec.).

IR (Nujol): 3250, 3150, 1770, 1670, 1610, 1590, 1510 cm$^{-1}$.

NMR (D$_2$O, δ): 1.29 (3H, t, J=7 Hz), 3.19 and 3.73 (2H, ABq, J=18 Hz), 3.37 and 3.50 (3H, s), 4.32 (2H, q, J=7 Hz), 5.28 (1H, d, J=5 Hz), 5.30 and 5.70 (2H, ABq, J=14 Hz), 5.87 (1H, d, J=5 Hz), 8.10 (1H, m), 8.4–9.0 (3H, m), 9.33 (1H, m).

EXAMPLE 2

The following compounds were obtained according to a similar manner to that of Example 1.

(1) 7-[2-Ethoxyimino-2-(5-amino-1,2,4-thiadiazol-3-yl)-acetamido]-3-(3-methylamino-1-pyridiniomethyl)-3-cephem-4-carboxylate (syn isomer), mp 149° to 157° C. (dec.).

IR (Nujol): 3250, 3050, 1770, 1660, 1610, 1530 cm$^{-1}$.

(2) 7-[2-Ethoxyimino-2-(5-amino-1,2,4-thiadiazol-3-yl)-acetamido]-3-(4-dodecanoyloxymethyl-1-pyridiniomethyl)-3-cephem-4-carboxylate (syn isomer), mp 111.5° to 118.0° C. (dec.).

IR (Nujol): 3300, 1770, 1730, 1670, 1640, 1610, 1570, 1520 cm$^{-1}$.

NMR (d$_6$-DMSO+D$_2$O, δ): 0.85 (3H, m), 1.25 (21H, m), 2.40 (2H, m), 3.40 (2H, m), 4.15 (2H, q, J=7 Hz), 4.80–5.93 (4H, m), 5.07 (1H, d, J=5 Hz), 5.71 (1H, d, J=5 Hz), 8.00 (2H, d, J=6 Hz), 9.22 (2H, d, J=6 Hz).

(3) 7-[2-Ethoxyimino-2-(5-amino-1,2,4-thiadiazol-3-yl)-acetamido]-3-(4-hexadecanoyloxymethyl-1-pyridiniomethyl)-3-cephem-4-carboxylate (syn isomer), mp 121° to 130° C. (dec.).

IR (Nujol): 3300, 3150, 1770, 1670, 1640, 1610, 1570, 1520 cm$^{-1}$.

NMR (d$_6$-DMSO+D$_2$O, δ): 0.82 (3H, m), 1.21 (29H, m), 2.35 (2H, m), 3.42 (2H, m), 4.15 (2H, q, J=7 Hz), 5.05 (1H, d, J=5 Hz), 5.2–5.6 (2H, m), 5.40 (2H, s), 5.70 (1H, d, J=5 Hz), 8.02 (2H, d, J=6 Hz), 9.28 (2H, d, J=6 Hz).

(4) Sodium 7-[2-ethoxyimino-2-(5-amino-1,2,4-thiadiazol-3-yl)acetamido]-3-(3-sulfonatomethylamino-1-pyridiniomethyl)-3-cephem-4-carboxylate (syn isomer), mp 161° to 169° C. (dec.).

IR (Nujol): 3350, 3300, 1760, 1660, 1640, 1610, 1530 cm$^{-1}$.

(5) 7-[2-Ethoxyimino-2-(5-amino-1,2,4-thiadiazol-3-yl)acetamido]-3-(3-dimethylamino-1-pyridiniomethyl)-3-cephem-4-carboxylate (syn isomer), mp 129° to 138° C. (dec.).

IR (Nujol): 3300, 1775, 1660, 1620, 1580, 1530 cm$^{-1}$.

(6) 7-[2-Ethoxyimino-2-(5-amino-1,2,4-thiadiazol-3-yl)acetamido]-3-[3-(2-hydroxyethyl)amino-1-pyridiniomethyl]-3-cephem-4-carboxylate (syn isomer), mp 141° to 150° C. (dec.).

IR (Nujol): 3300, 1770, 1660, 1610, 1530 cm$^{-1}$.

(7) 7-Ethoxyimino-2-(5-amino-1,2,4-thiadiazo-3-yl)-acetamido]-3-[3-{N-(2-hydroxyethyl)formamido}-1-pyridiniomethyl]-3-cephem-4-carboxylate (syn isomer), mp 147° to 155° C. (dec.).

IR (Nujol): 3250, 1770, 1670, 1610, 1530, 1510 cm$^{-1}$.

NMR (D$_2$O, δ): 1.36 (3H, t, J=7 Hz), 3.30 and 3.73 (2H, ABq, J=18 Hz), 3.70–4.30 (4H, m), 4.39 (2H, q, J=7 Hz), 5.35 (1H, d, J=5 Hz), 5.43 and 5.70 (2H, ABq, J=14 Hz), 5.95 (1H, d, J=5 Hz), 8.69 (1H, s), 8.80–8.85 (2H, m), 8.95 (1H, d, J=6 Hz), 9.37 (1H, s).

(8) 7-[2-Ethoxyimino-2-(5-amino-1,2,4-thiadiazol-3-yl)acetamido]-3-(3-sulfo-1-pyridiniomethyl)-3-cephem-4-carboxylate (syn isomer), mp 175° to 182° C. (dec.).

IR (Nujol): 3300, 3200, 3050, 1780, 1670, 1630, 1530 cm$^{-1}$.

NMR (D$_2$O+NaHCO$_3$, δ): 1.34 (3H, t, J=7 Hz), 3.30 and 3.73 (2H, ABq, J=18 Hz), 4.36 (2H, q, J=7 Hz), 5.32 (1H, d, J=5 Hz), 5.40 and 5.73 (2H, ABq, J=14 Hz), 5.92 (1H, d, J=5 Hz), 8.23 (1H, dd, J=6 and 8 Hz), 8.91 (1H, dd, J=8 and 1 Hz), 9.15 (1H, dd, J=1 and 6 Hz), 9.43 (1 H, broad s).

(9) 7-[2-Ethoxyimino-2-(5-amino-1,2,4-thiadiazol-3-yl)acetamido]-3-[4-(3-hexadecanoyloxypropyl)-1-pyridiniomethyl]-3-cephem-4-carboxylate (syn isomer), mp 140° to 150° C. (dec.).

IR (Nujol): 3300, 1775, 1725, 1670, 1640, 1610, 1525 cm$^{-1}$.

NMR (DMSO-d$_6$+D$_2$O, δ): 0.87 (3H, t, J=5 Hz), 1.25 (31H, m), 1.75–2.40 (2H, m), 2.67–3.23 (2H, m), 3.56 (2H, m), 3.80–4.40 (4H, m), 5.03 (1H, d, J=5 Hz), 4.9–5.7 (2H, m), 5.83 (1H, d, J=5 Hz), 7.98 (2H, d, J=7 Hz), 9.22 (2H, d, J=7 Hz)

(10) 7-[2-Ethoxyimino-2-(5-amino-1,2,4-thiadiazol-3-yl)acetamido]-3-(4-oleoyloxymethyl-1-pyridiniomethyl)-3-cephem-4-carboxylate (syn isomer), mp 106° to 116° C. (dec.).

IR (Nujol): 3300, 1770, 1670, 1640, 1610, 1520 cm$^{-1}$.
NMR (DMSO-d$_6$+D$_2$O, δ): 0.84 (3H, t, J=5 Hz), 1.25 (25H, m), 1.95 (4H, m), 2.41 (2H, m), 3.60 (2H, m), 4.15 (2H, q, J=7 Hz), 4.9–5.8 (6H, m), 5.07 (1H, d, J=5 Hz), 5.72 (1H, d, J=5 Hz), 8.04 (2H, d, J=6 Hz), 9.27 (2H, d, J=6 Hz)

EXAMPLE 3

To a suspension of 7-[2-ethoxyimino-2-(5-amino-1,2,4-thiadiazol-3-yl)acetamido]-3-[3-(N-methylformamido)-1-pyridiniomethyl]-3-cephem-4-carboxylate (syn isomer) (2.75 g) in methanol (27.5 ml) was added concentrated hydrochloric acid (1.39 ml) and the mixture was stirred for 75 minutes. The solvent was evaporated and the residue was triturated in acetone. The obtained powder was suspended in water (70 ml), adjusted to pH 4 to 5 with aqueous solution of sodium bicarbonate and subjected to column chromatography on a non ionic adsorption resin "Diaion HP 20" (Trademark: Prepared by Mitsubishi Chemical Industries) (100 ml). After the column was washed with water, the elution was carried out with 15% aqueous isopropyl alcohol. The eluates containing an object compound were collected, evaporated to remove isopropyl alcohol under reduced pressure and lyophilized to give 7-[2-ethoxyimino-2-(5-amino-1,2,4-thiadiazol-3-yl)acetamido]-3-(3-methylamino-1-pyridiniomethyl)-3-cephem-4-carboxylate (syn isomer) (1.41 g), mp 149° to 157° C. (dec.).

IR (Nujol): 3250, 3050, 1770, 1660, 1610, 1530 cm$^{-1}$.

NMR (DMSO-d$_6$+D$_2$O, δ): 1.22 (3H, t, J=7 Hz), 2.79 (3H, s), 3.05 and 3.57 (2H, ABq, J=18 Hz), 4.15 (2H, q, J=7 Hz), 5.05 (1H, d, J=5 Hz), 5.08 and 5.55 (2H, ABq, J=14 Hz), 5.70 (1H, d, J=5 Hz), 7.65 (2H, m), 8.40 (1H, m), 8.60 (1H, broad s).

EXAMPLE 4

The following compound was obtained according to a similar manner to that of Example 3.

7-[2-Ethoxyimino-2-(5-amino-1,2,4-thiadiazol-3-yl)acetamido]-3-[3-(2-hydroxyethyl)amino-1-pyridiniomethyl]-3-cephem-4-carboxylate (syn isomer), mp. 141° to 150° C. (dec.).

IR (Nujol): 3300, 1770, 1660, 1610, 1530 cm$^{-1}$.

NMR (D$_2$O, δ): 1.30 (3H, t, J=7 Hz), 3.44 (2H, t, J=5 Hz), 3.23 and 3.80 (2H, ABq, J=18 Hz), 3.80 (2H, t, J=5 Hz), 4.33 (2H, q, J=7 Hz), 5.28 (1H, d, J=5 Hz), 5.15 and 5.43 (2H, ABq, J=15 Hz), 5.88 (1H, d, J=5 Hz), 7.65 (2H, m), 7.97–8.30 (2H, m).

EXAMPLE 5

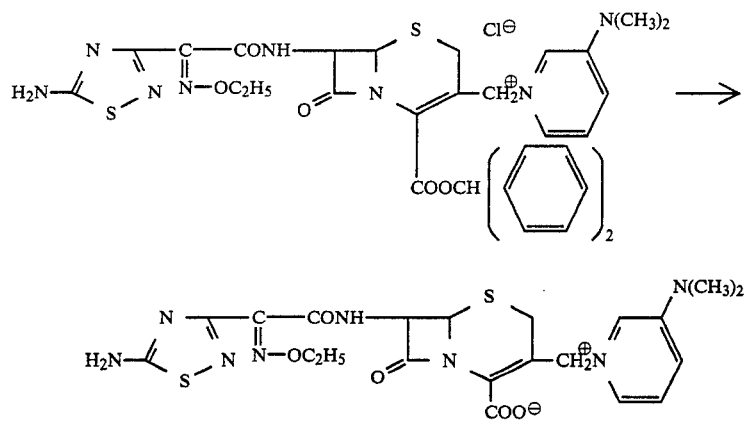

A mixture of diphenylmethyl 7-[2-ethoxyimino-2-(5-amino-1,2,4-thiadiazol-3-yl)acetamido]-3-(3-dimethylamino-1-pyridiniomethyl)-3-cephem-4-carboxylate chloride (syn isomer) (0.42 g) and anisole (1 ml) in trifluoroacetic acid (3.5 ml) was stirred for 15 minutes under cooling in an ice bath. The mixture was poured into diisopropyl ether (10 ml) and a resulting precipitate was filtered. The powder was dissolved in water and subjected to column chromatography on a non ionic adsorption resin "Diaion HP 20" (10 ml). After the column was washed with water, the elution was carried out with 30% aqueous methanol. The eluates containing an object compound were collected, evaporated to remove methanol under reduced pressure and lyophilized to give 7-[2-ethoxyimino-2-(5-amino-1,2,4-thiadiazol-3-yl)acetamido]-3-(3-dimethylamino-1-pyridiniomethyl)-3-cephem-4-carboxylate (syn isomer) (0.12 g), mp 129° to 138° C. (dec.).

IR (Nujol): 3300, 1775, 1660, 1620, 1580, 1530 cm$^{-1}$.

NMR (D$_2$O, δ): 1.30 (3H, t, J=7 Hz), 3.03 (6H, s), 3.20 and 3.60 (2H, ABq, J=18 Hz), 4.32 (2H, q, J=7 Hz), 5.26 (1H, d, J=5 Hz), 5.17 and 5.43 (2H, ABq, J=16 Hz), 5.83 (1H, d, J=5 Hz), 7.65 (2H, m), 8.00 (1H, m), 8.19 (1H, m).

EXAMPLE 6

The following compounds were obtained according to a similar manner to that of Example 5.

(1) 7-[2-Ethoxyimino-2-(5-amino-1,2,4-thiadiazol-3-yl)acetamido]-3-[3-(N-methylformamido)-1-pyridiniomethyl]-3-cephem-4-carboxylate (syn isomer), mp 120° to 127° C. (dec.).

IR (Nujol): 3250, 3150, 1770, 1670, 1610, 1590, 1510 cm$^{-1}$.

(2) 7-[2-Ethoxyimino-2-(5-amino-1,2,4-thiadiazol-3-yl)acetamido]-3-(3-methylamino-1-pyridiniomethyl)-3-cephem-4-carboxylate (syn isomer), mp 149° to 157° C. (dec.).

IR (Nujol): 3250, 3050, 1770, 1660, 1610, 1530 cm$^{-1}$.

(3) 7-[2-Ethoxyimino-2-(5-amino-1,2,4-thiadiazol-3-yl)acetamido]-3-(4-dodecanoyloxymethyl-1-pyridiniomethyl)-3-cephem-4-carboxylate (syn isomer), mp 111.5° to 118.0° C. (dec.).

IR (Nujol): 3300, 1770, 1730, 1670, 1640, 1610, 1570, 1520 cm$^{-1}$.

(4) 7-[2-Ethoxyimino-2-(5-amino-1,2,4-thiadiazol-3-yl)acetamido]-3-(4-hexadecanoyloxymethyl-1-pyridiniomethyl)-3-cephem-4-carboxylate (syn isomer), mp 121° to 130° C. (dec.).

IR (Nujol): 3300, 3150, 1770, 1670, 1640, 1610, 1570, 1520 cm$^{-1}$.

(5) Sodium 7-[2-Ethoxyimino-2-(5-amino-1,2,4-thiadiazol-3-yl)acetamido]-3-(3-sulfonatomethylamino-1-pyridiniomethyl)-3-cephem-4-carboxylate (syn isomer), mp 161° to 169° C. (dec.).

IR (Nujol): 3350, 3300, 1760, 1660, 1640, 1610, 1530 cm$^{-1}$.

(6) 7-[2-Ethoxyimino-2-(5-amino-1,2,4-thiadiazol-3-yl)acetamido]-3-[3-(2-hydroxyethyl)amino-1-pyridiniomethyl]-3-cephem-4-carboxylate (syn isomer), mp 141° to 150° C. (dec.).

IR (Nujol): 3300, 1770, 1660, 1610, 1530 cm$^{-1}$.

(7) 7-[2-Ethoxyimino-2-(5-amino-1,2,4-thiadiazol-3-yl)acetamido]-3-[3-{N-(2-hydroxyethyl)-formamido}-1-pyridiniomethyl]-3-cephem-4-carboxylate (syn isomer), mp 147° to 155° C. (dec.).

IR (Nujol): 3250, 1770, 1670, 1610, 1530, 1510 cm$^{-1}$.

(8) 7-[2-Ethoxyimino-2-(5-amino-1,2,4-thiadiazol-3-yl)acetamido]-3-(3-sulfo-1-pyridiniomethyl)-3-cephem-4-carboxylate (syn isomer), mp 175° to 182° C. (dec.).

IR (Nujol): 3300, 3200, 3050, 1780, 1670, 1630, 1530 cm$^{-1}$.

(9) 7-[2-Ethoxyimino-2-(5-amino-1,2,4-thiadiazol-3-yl)acetamido]-3-[4-(3-hexadecanoyloxypropyl)-1-pyridiniomethyl]-3-cephem-4-carboxylate (syn isomer), mp 140° to 150° C. (dec.).

IR (Nujol): 3300, 1775, 1725, 1670, 1640, 1610, 1525 cm$^{-1}$.

(10) 7-[2-Ethoxyimino-2-(5-amino-1,2,4-thiadiazol-3-yl)acetamido]-3-(4-oleoyloxymethyl-1-pyridiniomethyl)-3-cephem-4-carboxylate (syn isomer), mp 106° to 116° C. (dec.).

IR (Nujol): 3300, 1770, 1670, 1640, 1610, 1520 cm$^{-1}$.

PREPARATION 13

The following compounds were obtained according to a similar manner to that of Preparation 7.

(1) 4-Tetradecanoyloxymethylpyridine (oil).

IR (Film): 2910, 2850, 1740, 1606, 1560, 1460, 1405, 1160 cm$^{-1}$.

NMR (DMSO-d$_6$, δ): 0.7–1.9 (25H, m), 2.1–2.5 (2H, m), 5.12 (2H, s), 7.3 (2H, m), 8.5 (2H, m).

(2) 3-Hexadecanoyloxymethylpyridine (oil).

IR (Film): 2950, 2860, 1740, 1580, 1470, 1430, 1380, 1350, 1230, 1160, 1120, 1030 cm$^{-1}$.

NMR (DMSO-d$_6$, δ): 0.7–1.7 (29H, m), 2.35 (2H, t, J=7 Hz), 5.12 (2H, s), 7.36 (1H, m), 7.75 (1H, m), 8.50 (2H, m).

(3) 4-Octadecanoyloxymethylpyridine (semi solid).

IR (Nujol): 1740, 1605, 1560, 1415, 1160 cm$^{-1}$.

NMR (DMSO-d$_6$+D$_2$O, δ): 0.7–1.9 (33H, m), 2.1–2.6 (2H, m), 5.05 (2H, s), 7.15 (2H, m), 8.50 (2H, m).

PREPARATION 14

Sodium 7-[2-methoxyimino-2-(5-amino-1,2,4-thiadiazol-3-yl)acetamido]cephalosporanate (syn isomer) was obtained by reacting 7-[2-methoxyimino-2-(5-amino-1,2,4-thiadiazol-3-yl)acetamido]cephalosporanic acid (syn isomer) with sodium acetate in a conventional manner. mp 185° to 190° C. (dec.)

IR (Nujol): 3150, 1765, 1745, 1670, 1550, 1400, 1355, 1290, 1250, 1055 cm$^{-1}$.

EXAMPLE 7

The following compounds were obtained according to similar manners to those of aforesaid Examples.

(1) 7-[2-Ethoxyimino-2-(5-amino-1,2,4-thiadiazol-3-yl)-acetamido]-3-(3-methoxymethyl-1-pyridiniomethyl)-3-cephem-4-carboxylate (syn isomer), mp 138° to 146° C. (dec.).

IR (Nujol): 3250, 3150, 1770, 1670, 1610, 1530, 1340, 1280, 1230, 1190, 1140 cm$^{-1}$.

NMR (D$_2$O, δ): 1.30 (3H, t, J=7 Hz), 3.47 (3H, s), 3.20 and 3.66 (2H, ABq, J=18 Hz), 4.33 (2H, q, J=7 Hz), 4.73 (2H, s), 5.28 (1H, d, J=5 Hz), 5.34 and 5.63 (2H, ABq, J=14 Hz), 5.88 (1H, d, J=5 Hz), 8.15 (1H, m), 8.51 (1H, m), 8.90 (2H, m).

(2) 7-[2-Ethoxyimino-2-(5-amino-1,2,4-thiadiazol-3-yl)-acetamido]-3-[3-(N,N-dimethylaminomethyl)-1-pyridiniomethyl]-3-cephem-4-carboxylate (syn isomer). mp 145.5° to 155.5° C. (dec.).

IR (Nujol): 3300, 3150, 2700, 1770, 1660, 1610, 1520, 1350, 1290, 1145, 1060, 1030 cm$^{-1}$.

NMR (D$_2$O, δ): 1.33 (3H, t, J=7 Hz), 3.00 (6H, s), 3.33 and 3.77 (2H, ABq, J=18 Hz), 4.35 (2H, q, J=7 Hz), 4.60 (2H, s), 5.32 (1H, d, J=5 Hz), 5.43 and 5.67 (2H, ABq, J=14 Hz), 5.88 (1H, d, J=5 Hz), 8.24 (1H, m), 8.78 (1H, m), 9.17 (2H, m).

(3) 7-[2-Cyclopentyloxyimino)-2-(5-amino-1,2,4-thiadiazol-3-yl)acetamido]-3-[4-(1H-tetrazol-5-yl)-1-pyridiniomethyl]-3-cephem-4-carboxylate (syn isomer), mp. 181.5° to 190.0° C. (dec.).

IR (Nujol): 3300, 1775, 1670, 1640, 1530, 1400, 1350, 1210, 1160, 1060, 1000 cm$^{-1}$.

NMR (D$_2$O+NaHCO$_3$, δ): 1.1–1.9 (8H, m), 3.25 and 3.70 (2H, ABq, J=18 Hz), 5.30 (1H, d, J=5 Hz), 5.33 and 5.67 (2H, ABq, J=15 Hz), 5.84 (1H, d, J=5 Hz), 8.37 (2H, d, J=6 Hz), 8.98 (2H, d, J=6 Hz).

(4) 7-[2-(2-Cyclopenten-1-yloxyimino)-2-(5-amino-1,2,4-thiadiazol-3-yl)acetamido]-3-[4-(1H-tetrazol-5-yl)-1-pyridiniomethyl]-3-cephem-4-carboxylate (syn isomer), mp 165° to 174° C. (dec.).

IR (Nujol): 3300, 1770, 1670, 1635, 1530, 1210, 1160, 1110, 1060, 1030, 1010 cm$^{-1}$.

NMR (D$_2$O+NaHCO$_3$, δ): 1.6–2.5 (4H, m), 3.28 and 3.68 (2H, ABq, J=18 Hz), 5.12–6.20 (5H, m), 5.30 (1H, d, J=5 Hz), 5.88 (1H, d, J=5 Hz), 8.37 (2H, d, J=6 Hz), 8.98 (2H, d, J=6 Hz).

(5) 7-[2-Ethoxyimino-2-(5-amino-1,2,4-thiadiazol-3-yl)-acetamido]-3-(3-methylthiomethyl-1-pyridiniomethyl)-3-cephem-4-carboxylate (syn isomer), mp 150° to 153° C. (dec.).

IR (Nujol): 3300, 3150, 1770, 1660, 1640–1610, 1530, 1280, 1140, 1060, 1040 cm$^{-1}$.

NMR (D$_2$O, δ): 1.33 (3H, t, J=7 Hz), 2.03 (3H, s), 3.35 and 3.85 (2H, ABq, J=18 Hz), 3.97 (2H, s), 4.43 (2H, q, J=7 Hz), 5.40 (1H, d, J=5 Hz), 5.45 and 5.92 (2H, ABq, J=14 Hz), 5.95 (1H, d, J=5 Hz), 7.93–8.27 (1H, m), 8.62 (1H, broad d J=8 Hz), 8.87 (1H, d, J=5 Hz), 8.92 (1H, s).

(6) 7-[2-Ethoxyimino-2-(5-amino-1,2,4-thiadiazol-3-yl)-acetamido]-3-(4-methylthio-1-pyridiniomethyl)-3-cephem-4-carboxylate (syn isomer), mp 167° to 171° C. (dec.).

IR (Nujol): 3650–3100, 1770, 1660, 1620, 1530, 1490, 1280, 1170, 1100, 1030 cm$^{-1}$.

NMR (D$_2$O+DCl, δ): 1.32 (3H, t, J=7 Hz), 2.70 (3H, s), 3.33 and 3.83 (2H, ABq, J=18 Hz), 4.40 (2H, q, J=7 Hz), 5.37 (1H, d, J=5 Hz), 5.23 and 5.70 (2H, ABq, J=14 Hz), 5.95 (1H, d, J=5 Hz), 7.80 (2H, d, J=7 Hz), 8.57 (2H, d, J=7 Hz).

(7) 7-[2-Ethoxyimino-2-(5-amino-1,2,4-thiadiazol-3-yl)-acetamido]-3-(3-methoxy-1-pyridiniomethyl)-3-cephem-4-carboxylate (syn isomer), mp 137.5° to 145° C. (dec.).

IR (Nujol): 3250, 3150, 1770, 1665, 1610, 1530, 1510, 1290, 1240, 1180, 1150, 1110, 1040 cm$^{-1}$.

NMR (D$_2$O, δ): 1.22 (3H, t, J=7 Hz), 3.15 and 3.58 (2H, ABq, J=18 Hz), 3.94 (3H, s), 4.26 (2H, q, J=7 Hz), 5.22 (1H, d, J=5 Hz), 5.22 and 5.50 (2H, ABq, J=14 Hz), 5.82 (1H, d, J=5 Hz), 8.0 (1H, m), 8.57 (2H, m).

(8) 7-[2-Methoxyimino-2-(5-amino-1,2,4-thiadiazol-3-yl)acetamido]-3-(3-methoxymethyl-1-pyridiniomethyl)-3-cephem-4-carboxylate (syn isomer), mp 138° to 145.5° C. (dec.).

IR (Nujol): 3250, 3150, 1770, 1660, 1610, 1525, 1280, 1190, 1140, 1100, 1060, 1035 cm$^{-1}$.

NMR (D$_2$O, δ): 3.25 and 3.70 (2H, ABq, J=18 Hz), 3.50 (3H, s), 4.09 (3H, s), 4.78 (2H, s), 5.30 (1H, d, J=5 Hz), 5.38 and 5.65 (2H, ABq, J=15 Hz), 5.92 (1H, d, J=5 Hz), 8.10 (1H, m), 8.56 (1H, d, J=8 Hz), 8.95 (2H, m).

(9) 7-[2-Ethoxyimino-2-(5-amino-1,2,4-thiadiazol-3-yl)-acetamido]-3-[4-(1H-tetrazol-5-yl)-1-pyridiniomethyl]-3-cephem-4-carboxylate (syn isomer), mp 182° to 187° C. (dec.).

IR (Nujol): 3300, 3150, 1775, 1665, 1635, 1520, 1150, 1030 cm$^{-1}$.

NMR (D$_2$O+NaHCO$_3$, δ): 1.30 (3H, t, J=7 Hz), 3.32 and 3.75 (2H, ABq, J=18 Hz), 4.30 (2H, q, J=7 Hz), 5.38 (1H, d, J=5 Hz), 5.33 and 5.62 (2H, ABq, J=14 Hz) 5.97 (1H, d, J=5 Hz), 8.35 (2H, d, J=6 Hz), 8.93 (2H, d, J=6 Hz).

(10) 7-[2-Ethoxyimino-2-(5-amino-1,2,4-thiadiazol-3-yl)-acetamido]-3-[3-(1H-tetrazol-5-yl)-1-pyridiniomethyl]-3-cephem-4-carboxylate (syn isomer), mp 176° to 181° C. (dec.).

IR (Nujol): 3290, 3150, 1770, 1665, 1605, 1520, 1150, 1030 cm$^{-1}$.

NMR (D$_2$O+NaHCO$_3$, δ): 1.28 (3H, t, J=7 Hz), 3.42 and 3.80 (2H, ABq, J=18 Hz), 4.30 (2H, q, J=7 Hz), 5.32 (1H, d, J=5 Hz), 5.50 and 5.80 (2H, ABq, J=14 Hz), 5.97 (1H, d, J=5 Hz), 8.0–8.3 (1H, m), 8.8–9.2 (2H, m), 9.5 (1H, broad s)

(11) 7-[2-(2-Propynyloxyimino)-2-(5-amino-1,2,4-thiadiazol-3-yl)acetamido-3-[4-(1H-tetrazol-5-yl)-1-pyridiniomethyl]-3-cephem-4-carboxylate (syn isomer), mp 165° to 175° C. (dec.).

IR (Nujol): 3250, 1770, 1670, 1635, 1530, 1150, 1010 cm$^{-1}$.

NMR (DMSO-d$_6$, δ): 3.2–3.8 (2H, m), 3.5 (1H, m), 4.7 (2H, m), 5.18 (1H, d, J=5 Hz), 5.2–5.7 (2H, m), 5.89 (1H, dd, J=5 and 8 Hz), 8.10 (2H, broad s), 8.52 (2H, d, J=6 Hz), 8.88 (2H, d, J=6 Hz) 9.63 (1H, d, J=8 Hz).

(12) 7-[2-Ethoxyimino-2-(5-amino-1,2,4-thiadiazol-3-yl)-acetamido]-3-(3-mesylmethyl-1-pyridiniomethyl)-3-cephem-4-carboxylate (syn isomer), mp 155° to 158° C. (dec.).

IR (Nujol): 3300, 3150, 1770, 1660, 1610, 1530 cm$^{-1}$.

NMR (D$_2$O, δ): 1.30 (3H, t, J=7 Hz), 3.18 (3H, s), 3.15 and 3.70 (2H, ABq, J=18 Hz), 4.35 (2H, q, J=7 Hz), 4.87 (2H, s), 5.28 (1H, d, J=5 Hz), 5.33 and 5.68 (2H, ABq, J=14 Hz), 5.90 (1H, d, J=5 Hz), 8.0–8.3 (1H, m), 8.65 (1H, broad d, J=7 Hz), 9.0–9.3 (1H, m), 9.30 (1H, s).

(13) 7-[2-Methoxyimino-2-(5-amino-1,2,4-thiadiazol-3-yl)acetamido]-3-(4-hexadecanoyloxymethyl-1-pyridiniomethyl)-3-cephem-4-carboxylate (syn isomer), mp 143° to 148° C. (dec.).

IR (Nujol): 3270, 3150, 1770, 1750, 1730, 1670, 1640, 1610, 1520, 1145, 1135, cm$^{-1}$.

NMR (DMSO-d$_6$+D$_2$O, δ): 0.85 (3H, t, J=5 Hz), 1.0–1.9 (27H, m), 2.1–2.5 (2H, m), 3.1–3.7 (2H, m), 3.87 (3H, s), 5.07 (1H, d, J=5 Hz), 5.1–5.7 (2H, m), 5.40 (2H, broad s), 5.5–5.8 (1H, m), 8.10 (2H, m), 9.40 (2H, m).

(14) 7-[2-Ethoxyimino-2-(5-amino-1,2,4-thiadiazol-3-yl)-acetamido]-3-(4-tetradecanoyloxymethyl-1-pyridiniomethyl)-3-cephem-4-carboxylate (syn isomer), mp 149° to 154° C. (dec.).

IR (Nujol): 3260, 3150, 1770, 1670, 1640, 1610, 1525, 1150, 1035 cm$^{-1}$.

NMR (DMSO-d$_6$+D$_2$O, δ): 0.84 (3H, t, J=5 Hz), 1.3–1.7 (25H, m), 2.1–2.7 (2H, m), 3.20 and 3.58 (2H, ABq, J=18 Hz), 4.14 (2H, q, J=7 Hz), 5.08 (1H, d, J=5 Hz), 5.1–5.7 (4H, m), 5.73 (1H, d, J=5 Hz), 8.07 (2H, d, J=6 Hz), 9.41 (2H, d, J=6 Hz).

(15) 7-[2-Ethoxyimino-2-(5-amino-1,2,4-thiadiazol-3-yl)acetamido]-3-(4-octadecanoyloxymethyl-1-pyridiniomethyl)-3-cephem-4-carboxylate (syn isomer), mp 151° to 156° C. (dec.).

IR (Nujol): 3300, 3150, 1770, 1750, 1670, 1640, 1610, 1520 cm$^{-1}$.

NMR (DMSO-d$_6$+D$_2$O, δ): 0.85 (3H, t, J=5 Hz), 1.0–1.9 (33H, m), 2.1–2.5 (2H, m), 3.30 and 3.68 (2H, ABq, J=18 Hz), 4.14 (2H, q, J=7 Hz), 5.06 (1H, d, J=5 Hz), 5.0–5.8 (4H, m), 5.70 (1H, d, J=5 Hz), 8.07 (2H, d, J=6 Hz), 9.43 (2H, d, J=6 Hz).

(16) 7-[2-Methoxyimino-2-(5-amino-1,2,4-thiadiazol-3-yl)acetamido]-3-(4-oleoyloxymethyl-1-pyridiniomethyl)-3-cephem-4-carboxylate (syn isomer), mp 123° to 131° C. (dec.)

IR (Nujol): 3300, 1770, 1670, 1640, 1610, 1570, 1525 cm$^{-1}$.

NMR (DMSO-d$_6$+D$_2$O, δ): 0.80 (3H, t, J=5 Hz), 1.18 (22H, m), 1.6–2.4 (6H, m), 3.0–3.7 (2H, m), 3.80 (3H, s), 4.90–5.85 (6H, m), 5.06 (1H, d, J=5 Hz), 5.71 (1H, d, J=5 Hz), 8.02 (2H, m), 9.18 (2H, m).

(17) 7-[2-Ethoxyimino-2-(5-amino-1,2,4-thiadiazol-3-yl)acetamido]-3-(3-hexadecanoyloxymethyl-1-pyridiniomethyl)-3-cephem-4-carboxylate (syn isomer), mp 137° to 146° C. (dec.).

IR (Nujol): 3300, 3150, 1770, 1670, 1610, 1520, 1510 cm$^{-1}$.

NMR (DMSO-d$_6$+D$_2$O, δ): 0.82 (3H, t, J=6 Hz), 1.2 (29H, m), 2.32 (2H, m), 3.50 (2H, m), 4.15 (2H, q, J=7 Hz), 4.9–5.9 (4H, m), 5.06 (1H, d, J=5 Hz), 5.72 (1H, d, J=5 Hz), 8.13 (1H, m), 8.50 (1H, m), 9.30 (2H, m).

(18) 7-[2-Ethoxyimino-2-(5-amino-1,2,4-thiadiazol-3-yl)acetamido]-3-[3-(1H-tetrazol-5-ylthiomethyl)-1-pyridiniomethyl]-3-cephem-4-carboxylate (syn isomer), mp 151° to 160° C. (dec.).

IR (Nujol): 3250, 3150, 1775, 1670, 1620, 1525, 1140, 1030 cm$^{-1}$.

NMR (D$_2$O+NaHCO$_3$, δ): 1.27 (3H, t, J=7 Hz), 2.97 and 3.40 (2H, ABq, J=18 Hz), 4.32 (2H, q, J=7 Hz), 4.35 (2H, s), 5.27 and 5.50 (2H, ABq, J=14 Hz), 5.28 (1H, d, J=5 Hz), 5.88 (1H, d, J=5 Hz), 7.90 (1H, dd, J=6 and 8 Hz), 8.40 (1H, d, J=8 Hz), 8.75 (2H, m).

(19) 7-[2-Allyloxyimino-2-(5-amino-1,2,4-thiadiazol-3-yl)-acetamido]-3-[4-(1H-tetrazol-5-yl)-1-pyridiniomethyl]-3-cephem-4-carboxylate (syn isomer), mp 183° to 188° C. (dec.).

IR (Nujol): 3300, 3180, 1775, 1680, 1640, 1530, 1155, 1070, 1020 cm$^{-1}$.

NMR (D$_2$O+NaHCO$_3$, δ): 3.30 and 3.73 (2H, ABq, J=18 Hz), 4.5–5.1 (2H, m), 5.0–6.3 (5H, m), 5.35 (1H, d, J=5 Hz), 5.94 (1H, d, J=5 Hz), 8.22 (2H, d, J=6 Hz), 9.02 (2H, d, J=6 Hz).

PREPARATION 15

A mixture of 3-chloromethylpyridine hydrochloride (54.87 g) and thiosemicarbazide (27.68 g) in methanol (280 ml) was refluxed for 3.5 hours. Ater cooling, the mixture was diluted with methanol (220 ml) and the solution was poured into isopropyl alcohol (3 l) under stirring. The resulting precipitates were collected by filtration, washed with methanol and dried to give 3-(3-pyridylmethyl)isothiosemicarbazide dihydrochloride (58 g), mp 143°–145°. To a solution of the above obtained product (12.75 g) in water (100 ml) was dropped a solution of sodium nitrite (3.45 g) in water (25 ml) at 10° to 20° C. under stirring and cooling in an ice bath and followed by an addition of 10% hydrochloric acid (20 ml). The mixture was stirred for 40 minutes at 10° to 12° C. and then adjusted to pH 4.5 with an aqueous solution of sodium bicarbonate. The solution was evaporated to dryness and residue was extracted with ethanol. The extract was evaporated to dryness and the residue was triturated in acetone to give crude 3-(1H-tetrazol-5-ylthiomethyl)pyridine (10.44 g).

IR (Nujol): 2400–2300, 1605, 1570–1550, 1430, 1330, 1050, 1040 cm$^{-1}$.

NMR (D$_2$O, δ): 4.30 (2H, s), 7.50 (1H, dd, J=5 and 8 Hz) 8.10 (1H, m), 8.38 (2H, m).

The crude material was recrystallized from acetonitrile to give leaflet form. mp 141.5° to 144.0° C.

EXAMPLE 8

To a stirred mixture of 4-methoxypyridine (4.4 g), sodium iodide (36 g), phosphoric acid (1.2 g), water (6 ml) and acetonitrile (18 ml) was added sodium 7-[2-methoxyimino-2-(5-amino-1,2,4-thiadiazol-3-yl)-acetamido]cephalosporanate (syn isomer) (11.0 g) at 65° C. and the mixture was stirred for 2.5 hours at 68° to 70° C. The reaction mixture was poured into water (300 ml), adjusted to pH 3.2 with 3N hydrochloric acid and filtered. The filtrate was subjected to column chromatography on a non ionic adsorption resin "Diaion HP-20" (300 ml). After the column was washed with water (1 l), the elution was carried out with 30% aqueous methanol (700 ml). The eluate was concentrated to a weight of 17 g under reduced pressure and dissolved in N,N-dimethylformamide (17 ml). The solution was poured into acetone (200 ml) under stirring and the resulting precipitates were collected by filtration, washed with acetone and redissolved in warm water (100 ml). After an insoluble material was filtered off, the filtrate was passed through a column packed with acidic alumina (38 g), concentrated to a weight of 5.5 g under reduced pressure and dissolved in N,N-dimethylformamide (5 ml). The solution was poured into acetone (100 ml) under stirring and the resulting precipitates were collected by filtration, washed with acetone and dried to give 7-[2-methoxyimino-2-(5-amino-1,2,4-thiadiazol-3-yl)acetamido]-3-(4-methoxy-1-pyridiniomethyl)-3-cephem-4-carboxylate (syn isomer) (2.5 g), mp 180° to 185° C. (dec.).

IR (Nujol): 3300, 1760, 1670, 1640, 1610, 1560, 1520 cm$^{-1}$.

NMR (D$_2$O+CD$_3$OD, δ): 3.27 and 3.67 (2H, ABq, J=18 Hz), 4.12 (3H, s), 4.20 (3H, s), 5.28 (1H, d, J=4 Hz), 5.17 and 5.47 (2H, ABq, J=14 Hz), 5.93 (1H, d, J=4 Hz), 7.57 (2H, d, J=7 Hz), 8.83 (2H, d, J=7 Hz).

EXAMPLE 9

The following compounds were obtained according to similar manners to those of aforesaid Examples.

(1) 7-[2-Ethoxyimino-2-(5-amino-1,2,4-thiadiazol-3-yl)-acetamido]-3-(4-methoxy-1-pyridiniomethyl)-3-cephem-4-carboxylate (syn isomer), mp. 195° to 200° C. (dec.).

IR (Nujol): 3300, 1770, 1670, 1630, 1590, 1560 cm$^{-1}$.

NMR (D$_2$O+DCl, δ): 1.30 (3H, t, J=7 Hz), 3.40 and 3.73 (2H, ABq, J=18 Hz), 4.17 (3H, s), 4.42 (2H, q, J=7 Hz), 5.27 and 5.63 (2H, ABq, J=14 Hz), 5.33 (1H, d, J=4 Hz), 5.90 (1H, d, J=4 Hz), 7.50 (2H, d, J=8 Hz), 8.70 (2H, d, J=8 Hz).

(2) 7-[2-(2-Propynyloxyimino)-2-(5-amino-1,2,4-thiadiazol-3-yl)acetamido]-3-(4-methoxy-1-pyridiniomethyl)-3-cephem-4-carboxylate (syn isomer), mp. 185° to 190° C. (dec.).

IR (Nujol): 3250, 1770, 1740, 1640, 1570, 1520 cm$^{-1}$.

NMR (D$_2$O+DCl, δ): 3.08 (1H, t, J=2 Hz), 3.43 and 3.73 (2H, ABq, J=18 Hz), 4.17 (3H, s), 5.37 (1H, d, J=4 Hz), 5.40 (2H, d, J=2 Hz), 5.55 and 5.67 (2H, ABq, J=14 Hz), 5.93 (1H, d, J=4 Hz), 7.53 (2H, d, J=7 Hz), 8.73 (2H, d, J=7 Hz).

(3) 7-[2-Allyloxyimino-2-(5-amino-1,2,4-thiadiazol-3-yl)acetamido]-3-(4-methoxy-1-pyridiniomethyl)-3- cephem-4-carboxylate (syn isomer), mp. 180° to 185° C. (dec.).

IR (Nujol): 3300, 1780, 1660, 1640, 1620, 1570, 1520 cm$^{-1}$.

NMR (D$_2$O, δ): 3.20 and 3.57 (2H, ABq, J=18 Hz), 4.10 (3H, s), 4.5–4.8 (2H, m), 5.1–5.7 (5H, m), 5.85 (1H, d, J=4 Hz), 5.76–6.17 (1H, m), 7.45 (2H, d, J=7 Hz), 8.68 (2H, d, J=7 Hz).

(4) 7-[2-Ethoxyimino-2-(5-amino-1,2,4-thiadiazol-3-yl)acetamido]-3-(4-ethoxy-1-pyridiniomethyl)-3-cephem-4-carboxylate (syn isomer), mp. 150° to 155° C. (dec.).

IR (Nujol): 3350, 3250, 3150, 1770, 1670, 1635, 1610, 1555, 1515 cm$^{-1}$.

NMR (D$_2$O, δ): 1.30 (3H, t, J=7 Hz), 1.47 (3H, t, J=7 Hz), 3.23 and 3.63 (2H, ABq, J=18 Hz), 4.33 (2H, q, J=7 Hz), 4.42 (2H, q, J=7 Hz), 5.27 (1H, d, J=4 Hz), 5.18 and 5.35 (2H, ABq, J=14 Hz), 5.87 (1H, d, J=4 Hz), 7.42 (2H, d, J=7 Hz), 8.68 (2H, d, J=7 Hz).

(5) 7-[2-Methoxyimino-2-(5-amino-1,2,4-thiadiazol-3-yl)acetamido]-3-(3-methyl-4-methoxy-1-pyridiniomethyl)-3-cephem-4-carboxylate (syn isomer), mp. 140° to 145° C. (dec.).

IR (Nujol): 3250, 3150, 1770, 1660, 1635, 1610, 1515, 1490 cm$^{-1}$.

NMR (CD$_3$OD+D$_2$O, δ): 2.30 (3H, s), 3.15 and 3.62 (2H, ABq, J=18 Hz), 4.03 (3H, s), 4.18 (3H, s), 5.20 (1H, d, J=4 Hz), 5.12 and 5.45 (2H, ABq, J=14 Hz), 5.87 (1H, d, J=4 Hz), 7.50 (1H, d, J=7 Hz), 8.72 (1H, s), 8.83 (1H, d, J=7 Hz).

(6) 7-[2-Ethoxyimino-2-(5-amino-1,2,4-thiadiazol-3-yl)acetamido]-3-(3-methyl-4-methoxy-1-pyridiniomethyl)-3-cephem-4-carboxylate (syn isomer), mp. 155° to 160° C. (dec.).

IR (Nujol): 3250, 3150, 1770, 1665, 1630, 1610, 1515, 1490 cm$^{-1}$.

NMR (D$_2$O, δ): 1.32 (3H, t, J=7 Hz), 2.28 (3H, s), 3.20 and 3.62 (2H, ABq, J=18 Hz), 4.15 (3H, s), 4.35 (2H, q, J=7 Hz), 5.15 and 5.32 (2H, ABq, J=14 Hz), 5.28 (1H, d, J=4 Hz), 5.87 (1H, d, J=4 Hz), 7.43 (1H, d, J=7 Hz), 8.50 (1H, s), 8.62 (1H, d, J=7 Hz).

(7) 7-[2-Methoxyimino-2-(5-amino-1,2,4-thiadiazol-3-yl)acetamido]-3-(4-methylthio-1-pyridiniomethyl)-3-cephem-4-carboxylate (syn isomer), mp. 170° to 175° C. (dec.).

IR (Nujol): 3300, 3160, 3100, 1770, 1670, 1625, 1545, 1530, 1490 cm$^{-1}$.

NMR (D$_2$O+CD$_3$OD, δ): 2.70 (3H, s), 3.18 and 3.60 (2H, ABq, J=18 Hz), 4.03 (3H, s), 5.22 (1H, d, J=5 Hz), 5.13 and 5.42 (2H, ABq, J=14 Hz), 5.85 (1H, d, J=5 Hz), 7.78 (2H, d, J=7 Hz), 8.65 (2H, d, J=7 Hz).

(8) 7-[2-Allyloxyimino-2-(5-amino-1,2,4-thiadiazol-3-yl)acetamido]-3-(4-methylthio-1-pyridiniomethyl)-3-cephem-4-carboxylate (syn isomer), mp. 155° to 163° C. (dec.).

IR (Nujol): 3300, 1770, 1670, 1620, 1530, 1490 cm$^{-1}$.

NMR (DMSO-d$_6$, δ): 2.70 (3H, s), 3.08 and 3.52 (2H, ABq, J=18 Hz), 4.62 (2H, d, J=5 Hz), 5.03 and 5.47 (2H, ABq, J=14 Hz), 5.04 (1H, d, J=5 Hz), 5.2–6.2 (4H, m), 7.93 (2H, d, J=6 Hz), 8.17 (2H, broad s), 9.10 (2H, d, J=6 Hz), 9.49 (1H, d, J=8 Hz).

(9) 7-[2-Carboxymethoxyimino-2-(5-amino-1,2,4-thiadiazol-3-yl)acetamido]-3-(4-methylthio-1-pyridiniomethyl)-3-cephem-4-carboxylate (syn isomer), mp. 168° to 177° C. (dec.).

IR (Nujol): 3300, 1770, 1670, 1625, 1520, 1490 cm$^{-1}$.

NMR (DMSO-d$_6$+D$_2$O, δ): 2.70 (3H, s), 3.10 and 3.57 (2H, ABq, J=17 Hz), 5.10 (1H, d, J=5 Hz), 5.03 and 5.47 (2H, ABq, J=14 Hz), 5.77 (1H, d, J=5 Hz), 7.87 (2H, d, J=7 Hz), 8.88 (2H, d, J=7 Hz).

(10) 7-[2-Ethoxyimino-2-(5-amino-1,2,4-thiadiazol-3-yl)acetamido]-3-[4-(2-methoxyethoxy)methyl-1-pyridiniomethyl]-3-cephem-4-carboxylate (syn isomer), mp. 132° to 140° C. (dec.).

IR (Nujol): 3250, 1775, 1670, 1640, 1570, 1530 cm$^{-1}$.

NMR (D$_2$O, δ): 1.27 (3H, t, J=7 Hz), 3.37 (3H, s), 3.20 and 3.63 (2H, ABq, J=18 Hz), 3.74 (4H, m), 4.31 (2H, q, J=7 Hz), 4.90 (2H, s), 5.25 (1H, d, J=5 Hz), 5.30 and 5.57 (2H, ABq, J=14 Hz), 5.85 (1H, d, J=5 Hz), 8.01 (2H, d, J=7 Hz), 8.89 (2H, d, J=7 Hz).

(11) 7-[2-Methoxyimino-2-(5-amino-1,2,4-thiadiazol-3-yl)acetamido]-3-[4-(2-methoxyethoxy)methyl-1-pyridiniomethyl]-3-cephem-4-carboxylate (syn isomer), mp. 127° to 134° C. (dec.).

IR (Nujol): 3250, 1770, 1660, 1640, 1610, 1530 cm$^{-1}$.

NMR (D$_2$O, δ): 3.40 (3H, s), 3.22 and 3.63 (2H, ABq, J=18 Hz), 3.75 (4H, broad s), 4.05 (3H, s), 4.91 (2H, s), 5.26 (1H, d, J=5 Hz), 5.30 and 5.57 (2H, ABq, J=15 Hz), 5.87 (1H, d, J=5 Hz), 8.03 (2H, d, J=7 Hz), 8.90 (2H, d, J=7 Hz).

(12) 7-[2-Allyloxyimino-2-(5-amino-1,2,4-thiadiazol-3-yl)acetamido]-3-[4-(2-methoxyethoxy)methyl-1-pyridiniomethyl]-3-cephem-4-carboxylate (syn isomer), mp. 140° to 146° C. (dec.).

IR (Nujol): 3250, 1770, 1670, 1640, 1610, 1530 cm$^{-1}$.

NMR (D$_2$O, δ): 3.43 (3H, s), 3.27 and 3.67 (2H, ABq, J=18 Hz), 3.80 (4H, broad s), 4.96 (2H, s), 4.8–5.0 (2H, m), 5.0–5.6 (2H, m) 5.23 (1H, d, J=5 Hz), 5.27 and 5.50 (2H, ABq, J=14 Hz), 5.92 (1H, d, J=5 Hz), 5.9–6.1 (1H, m), 8.10 (2H, d, J=7 Hz), 8.95 (2H, d, J=7 Hz)

(13) 7-[2-Ethoxyimino-2-(5-amino-1,2,4-thiadiazol-3-yl)acetamido]-3-[4-(1H-tetrazol-5-ylthiomethyl)-1-pyridiniomethyl]-3-cephem-4-carboxylate (syn isomer), mp. 165° to 172° C. (dec.).

IR (Nujol): 3300, 3180, 1770, 1660, 1635, 1520 cm$^{-1}$.

NMR (D$_2$O+NaHCO$_3$, δ): 1.27 (3H, t, J=7 Hz), 3.10 and 3.55 (2H, ABq, J=18 Hz), 4.30 (2H, q, J=7 Hz), 4.70 (2H, s), 5.25 (1H, d, J=5 Hz), 5.23 and 5.50 (2H, ABq, J=14 Hz), 5.87 (1H, d, J=5 Hz), 7.79 (2H, d, J=7 Hz), 8.74 (2H, d, J=7 Hz).

(14) 7-[2-(2-Cyclopenten-1-yloxyimino)-2-(5-amino-1,2,4-thiadiazol-3-yl)acetamido]-3-[4-(1H-tetrazol-5-ylthiomethyl)-1-pyridiniomethyl]-3-cephem-4-carboxylate (syn isomer), mp. 173° to 180° C. (dec.).

IR (Nujol): 3300, 3150, 3050, 1770, 1660, 1630, 1530 cm$^{-1}$.

NMR (D$_2$O+NaHCO$_3$, δ): 1.70–2.60 (4H, m), 3.08 and 3.57 (2H, ABq, J=17 Hz), 4.73 (2H, s), 4.88–5.75 (3H, m), 5.27 (1H, d, J=5 Hz), 5.88 (1H, d, J=5 Hz), 5.75–6.35 (2H, m), 7.88 (2H, d, J=6 Hz), 8.81 (2H, d, J=6 Hz).

(15) 7-[2-Ethoxyimino-2-(5-amino-1,2,4-thiadiazol-3-yl)acetamido]-3-[4-(1H-tetrazol-5-ylthio)-1-pyridiniomethyl]-3-cephem-4-carboxylate (syn isomer), mp. 166° to 173° C. (dec.).

IR (Nujol): 3300, 3150, 1770, 1660, 1620, 1530, 1490 cm$^{-1}$.

NMR (D$_2$O+NaHCO$_3$, δ): 1.32 (3H, t, J=7 Hz), 3.33 and 3.67 (2H, ABq, J=18 Hz), 4.36 (2H, q, J=7 Hz), 5.23 and 5.50 (2H, ABq, J=14 Hz), 5.32 (1H, d, J=5 Hz), 5.94 (1H, d, J=5 Hz), 5.94 (1H, d, J=5 Hz), 7.57 (2H, d, J=7 Hz), 8.67 (2H, d, J=7 Hz).

(16) 7-[2-(2-Cyclopenten-1-yloxyimino)-2-(5-amino-1,2,4-thiadiazol-3-yl)acetamido]-3-[4-(1H-tetrazol-5-ylthio)-1-pyridiniomethyl]-3-cephem-4-carboxylate (syn isomer), mp. 164° to 171° C. (dec.).

IR (Nujol): 3300, 3150, 1770, 1670, 1620, 1530, 1490 cm$^{-1}$.

NMR (D$_2$O+NaHCO$_3$, δ): 1.80–2.60 (4H, m), 2.8–3.8 (2H, m), 5.10–5.65 (3H, m), 5.1–5.9 (4H, m), 5.30 (1H, d, J=5 Hz), 5.90 (1H, d, J=5 Hz), 6.15 (1H, m), 7.58 (2H, d, J=7 Hz), 8.70 (2H, d, J=7 Hz).

(17) 7-[2-Allyloxyimino-2-(5-amino-1,2,4-thiadiazol-3-yl)acetamido]-3-[4-(1H-tetrazol-5-yl)-1-pyridiniomethyl]-3-cephem-4-carboxylate (syn isomer), mp. 151° to 160° C. (dec.).

IR (Nujol): 3300, 1770, 1670, 1640, 1525 cm$^{-1}$.

NMR (D$_2$O+NaHCO$_3$, δ): 3.30 and 3.70 (2H, ABq, J=18 Hz), 4.5–4.8 (2H, m), 5.0–6.2 (7H, m), 8.37 (2H, d, J=6 Hz), 8.95 (2H, d, J=6 Hz).

(18) 7-[2-Ethoxyimino-2-(5-amino-1,2,4-thiadiazol-3-yl)acetamido]-3-[4-(2-methoxyethoxy)-1-pyridiniomethyl]-3-cephem-4-carboxylate (syn isomer), mp. 150° to 155° C. (dec.).

IR (Nujol): 3350, 3250, 3110, 1770, 1660, 1630, 1610, 1560, 1515 cm$^{-1}$.

NMR (D$_2$O, δ): 1.32 (3H, t, J=7 Hz), 3.45 (3H, s), 3.23 and 3.63 (2H, ABq, J=18 Hz), 3.77–4.07 (2H, m), 4.33 (2H, q, J=7 Hz), 4.4–4.7 (2H, m), 5.30 (1H, d, J=5 Hz), 5.22 and 5.37 (2H, ABq, J=14 Hz), 5.88 (1H, d, J=5 Hz), 7.50 (2H, d, J=7 Hz), 8.75 (2H, d, J=7 Hz).

(19) 7-[2-Ethoxyiminio-2-(5-amino-1,2,4-thiadiazol-3-yl)acetamido]-3-[4-(2-hydroxyethoxy)-1-pyridiniomethyl]-3-cephem-4-carboxylate (syn isomer), mp. 160° to 165° C. (dec.).

IR (Nujol): 3360, 3250, 3160, 1770, 1660, 1635, 1610, 1560, 1520 cm$^{-1}$.

NMR (D$_2$O, δ): 1.30 (3H, t, J=7 Hz), 3.20 and 3.58 (2H, ABq, J=18 Hz), 3.98 (2H, t, J=4 Hz), 4.28 (2H, q, J=7 Hz), 4.40 (2H, t, J=4Hz), 5.22 (1H, d, J=4 Hz), 5.12 and 5.30 (2H, ABq, J=14 Hz), 5.80 (1H, d, J=4 Hz), 7.40 (2H, d, J=7 Hz), 8.60 (2H, d, J=7 Hz).

(20) 7-[2-Ethoxyimino-2-(5-amino-1,2,4-thiadiazol-3-yl)acetamido]-3-[4-(2-methyl-5-oxo-6-hydroxy-2,5-dihydro-1,2,4-triazin-3-yl)thiomethyl-1-pyridiniomethyl]-3-cephem-4-carboxylate (syn isomer), mp. 195° to 197° C. (dec.).

IR (Nujol): 3300, 3180, 1773, 1665, 1655, 1635, 1610, 1510 cm$^{-1}$.

NMR (D$_2$O, δ): 1.28 (3H, t, J=7 Hz), 3.16 and 3.58 (2H, ABq, J=18 Hz), 3.66 (3H, s), 4.30 (2H, q, J=7 Hz), 5.22 (1H, d, J=5 Hz), 5.28 and 5.47 (2H, ABq, J=14 Hz), 5.83 (1H, d, J=5 Hz), 8.10 (2H, d, J=7 Hz), 8.82 (2H, d, J=7 Hz).

(21) 7-[2-(2-Cyclopenten-1-yloxyimino)-2-(5-amino-1,2,4-thiadiazol-3-yl)acetamido]-3-[4-(2-methyl-5-oxo-6-hydroxy-2,5-dihydro-1,2,4-triazin-3-yl)-thiomethyl-1-pyridiniomethyl]-3-cephem-4-carboxylate (syn isomer), mp. 168° to 173° C. (dec.).

IR (Nujol): 3300, 3150, 1770, 1635, 1510 cm$^{-1}$.

NMR (DMSO-d$_6$+D$_2$O, δ): 1.6–2.6 (4H, m), 3.58 (3H, s), 3.2–3.9 (2H, m), 5.1–6.1 (7H, m), 8.1 (2H, m), 8.8 (2H, m).

(22) 7-[2-Ethoxyimino-2-(5-amino-1,2,4-thiadiazol-3-yl)acetamido]-3-(4-methoxymethyl-1-pyridiniomethyl)-3-cephem-4-carboxylate (syn isomer), mp. 145° to 153° C. (dec.).

IR (Nujol): 3300, 1775, 1670, 1640, 1610, 1570, 1530 cm$^{-1}$.

NMR (D$_2$O, δ): 1.30 (3H, t, J=7 Hz), 3.50 (3H, s), 3.23 and 3.63 (2H, ABq, J=18 Hz), 4.32 (2H, q, J=7 Hz), 4.83 (2H, s), 5.28 (1H, d, J=5 Hz), 5.32 and 5.57 (2H, ABq, J=14 Hz), 5.88 (1H, d, J=5 Hz), 8.00 (2H, d, J=7 Hz), 8.90 (2H, d, J=7 Hz).

PREPARATION 16

To a solution of sodium (9.96 g) in 2-methoxyethanol (100 ml) was added dropwise 4-chloropyridine (42.7 g) under heating at 140° to 145° C. and stirring, which was continued for one hour at 135° C. after the addition. The mixture was cooled to −15° C. and dry ice (5.6 g) was added thereto. The mixture was warmed to 45° C. and then allowed to stand at room temperature. The resulting precipitates were removed by filtration and washed with diisopropyl ether. The filtrate and washings were combined and evaporated. The residual oil was distilled to give 4-(2-methoxyethoxy)pyridine (42.3 g), bp. 98° to 106° C. at 6 mmHg.

NMR (CDCl$_3$, δ): 3.42 (3H, s), 3.57–3.90 (2H, m), 4.03–4.30 (2H, m), 6.82 (2H, d, J=6 Hz), 8.60 (2H, d, J=6 Hz).

PREPARATION 17

To a solution of sodium (9.2 g) in ethylene glycol (100 ml) was added portionwise 4-chloropyridine (39.6 g) under heating at 120° to 130° C. and stirring, which was continued for one hour at 130° C. after the addition. The mixture was cooled to −15° C. and dry ice (5.2 g) was added thereto. The mixture was warmed to 45° C. and allowed to stand at room temperature. The resulting precipitates were removed by filtration and washed with diisopropyl ether. The filtrate and washings were combined and evaporated. The residual oil was distilled to give 4-(2-hydroxyethoxy)pyridine (9 g), bp. 138° to 145° C. at 5 to 6 mmHg, which solidified and recrystallized from ethyl acetate. mp. 113° to 115° C. (dec.).

NMR (DMSO-d$_6$+D$_2$O, δ): 3.82 (2H, t, J=5 Hz), 4.17 (2H, t, J=5 Hz), 7.02 (2H, d, J=6 Hz), 8.42 (2H, d, J=6 Hz).

PREPARATION 18

A mixture of 2-methyl-3-mercapto-5-oxo-6-hydroxy-2,5-dihydro-1,2,4-triazine (15.91 g), 4-chloromethylpyridine hydrochloride (19.68 g) and sodium bicarbonate (33.6 g) in water (500 ml) was stirred for 2 hours at 45° C. The mixture was cooled to 10° C. and adjusted to pH 6.2 with 6N hydrochloric acid. The resulting precipitates were collected by filtration, washed with water and acetone, and dried to give 2-methyl-3-(4-pyridylmethylthio)-5-oxo-6-hydroxy-2,5-dihydro-1,2,4-triazine (17.2 g), mp. 219° to 222° C. (dec.).

IR (nujol): 3480, 3400, 1700, 1630, 1605, 1500 cm$^{-1}$.

NMR (DMSO-d$_6$+D$_2$O, δ): 3.63 (3H, s), 4.43 (2H, s), 7.3–7.6 (2H, m), 8.4–8.6 (2H, m).

PREPARATION 19

To a solution of sodium (7.57 g) in 2-methoxyethanol (135 ml) was added dropwise a solution of 4-chloromethylpyridine hydrochloride (22.5 g) in 2-methoxyethanol (150 ml) under cooling in an ice-salt bath and stirring. The mixture was stirred for 45 minutes at 65° C. and evaporated under reduced pressure. The residue was dissolved in water (500 ml) and the solution was extracted with chloroform. The extract was washed with a saturated aqueous solution of sodium chloride, dried over magnesium sulfate and evaporated. The residual oil was distilled to give 4-(2-methoxyethoxymethyl)pyridine (21.56 g), bp 98° to 101° C. at 3 to 3.5 mmHg.

NMR (CDCl$_3$, δ): 3.42 (3H, s), 3.66 (4H, s), 4.63 (2H, s), 7.33 (2H, m), 8.63 (2H, m).

PREPARATION 20

(1) A mixture of 4-chloromethylpyridine hydrochloride (0.82 g) and thiosemicarbazide (0.46 g) in methanol (6 ml) was refluxed for 2 hours. The mixture was poured into isopropyl alcohol (60 ml) under vigorous stirring and the resulting precipitates were collected by filtration, washed with isopropyl alcohol and dried to give 3-(4-pyridylmethyl)isothiosemicarbazide dihydrochloride (0.75 g), mp. 185° to 188° C. (dec.).

IR (nujol): 3250, 3100, 2650, 1640, 1630, 1610, 1590, 1520, 1505 cm$^{-1}$.

(2) To a solution of 3-(4-pyridylmethyl)isothiosemicarbazide dihydrochloride (25.5 g) in water (180 ml) was added dropwise a solution of sodium nitrite (8.97 g) in water (50 ml) at 10° C. to 20° C. (under stirring and cooling in an ice-salt bath. To the reaction mixture was added dropwise 10% hydrochloric acid at 12° to 13° C. under stirring. The solution was adjusted to pH 4.7 with aqueous sodium bicarbonate and evaporated to dryness. To the residue was added ethanol and an insoluble material was removed by filtration. The filtrate was evaporated to give a dark brown oil, which was mixed with a solution of anhydrous sodium acetate (4.15 g) in methanol (250 ml).

The mixture was evaporated to dryness and the residue was triturated in diethyl ether to give sodium salt of 5-(4-pyridylmethylthio)tetrazole (8.61 g), which was used for next reaction without further purification. A solution of the said sodium salt in water was adjusted to pH 4 with aqueous sodium bicarbonate, salted out and extracted with tetrahydrofuran. The extract was dried over magnesium sulfate and evaporated to dryness. The residue was dissolved in ethanol and an insoluble material was removed by filtration. The filtrate was evaporated to dryness and the residue was crystallized from diethyl ether to give 5-(4-pyridylmethylthio)tetrazole, mp. 131° to 138° C. (dec.).

IR (nujol): 2450, 1940, 1610, 1510 cm$^{-1}$
NMR (D$_2$O+NaHCO$_3$, δ): 4.27 (2H, s), 7.33 (2H, d, J=5 Hz), 8.45 (2H, d, J=5 Hz).

PREPARATION 21

A mixture of 4-chloropyridine hydrochloride (7.25 g), 5-mercapto-1H-tetrazole (4.93 g) and triethylamine (14.64 g) in dimethylformamide (120 ml) was stirred for one hour at 82° to 85° C. and then cooled in an ice bath. The resulting precipitates were removed by filtration and the filtrate was mixed with water (60 ml). The aqueous solution was adjusted to pH 2 with 2N hydrochloric acid and evaporated to dryness under reduced pressure. The residue was triturated in chloroform (300 ml) and the resulting precipitates were collected by filtration and washed with the same solvent. To the precipitates was added ethanol (650 ml) and an insoluble material was removed by filtration. The filtrate was evaporated to dryness to give 4-(1H-tetrazol-5-ylthio)pyridine (4.03 g), mp. 159° to 161° C. (dec.).

IR (nujol): 3080, 2750–2300, 1630, 1610, 1510 cm$^{-1}$.
NMR (D$_2$O, δ): 7.70 (2H, d, J=7 Hz), 8.55 (2H, d, J=7 Hz).

PREPARATION 22

(i) 3-Mercaptopyridine hexachlorostannate and 2-hydroxyethyl bromide were reacted according to a conventional manner to give 3-(2-hydroxyethylthio)pyridine, oil.

I.R. (Film): 3250, 2940, 2860, 1575, 1565, 1470, 1410, 1110, 1070, 1045, 1020, 795 cm$^{-1}$.

N.M.R.(d$_6$-acetone, δ): 3.17(2H,t,J=7 Hz), 3.75(2H,t,J=7 Hz), 7.27(1H,m), 7.80(1H,m), 8.38(1H, dd, J=2 and 6 Hz), 8.55(1H,d,J=2 Hz).

(ii) 3-Mercaptopyridine hexachlorostannate and 2-dimethylaminoethyl chloride were reacted in a conventional manner to give 3-(2-dimethylaminoethylthio)pyridine, oil.

I.R.(Film): 3400, 3020, 2950, 2930, 2850, 2800, 2760, 1560, 1460, 1400, 1365 cm$^{-1}$.

N.M.R.(CDCl$_3$, δ): 2.23(6H, broad s), 2.37–2.70(2H,m), 2.87–3.20(2H,m), 7.0–7.33(1H,m), 7.53–7.80(1H,m), 8.30–8.50(1H,m), 8.57(1H,d, J=2 Hz).

EXAMPLE 10

The following compounds were obtained according to similar manners to those of aforesaid Examples.

(1) 7-[2-Ethoxyimino-2-(5-amino-1,2,4-thiadiazol-3-yl)acetamido]-3-[3-(2-hydroxyethylthio)-1-pyridiniomethyl]-3-cephem-4-carboxylate (syn isomer). m.p. 158° to 163° C. (dec.).

I.R.(Nujol): 3300, 3150, 1770, 1660, 1610, 1530, 1350, 1285, 1160, 1060, 1040 cm$^{-1}$.

N.M.R.(DCl+D$_2$O, δ): 1.33(3H,t,J=7 Hz), 3.37 and 3.85(2H,AB$_q$,J=18 Hz), 3.35(2H,t,J=6 Hz), 3.87(2H,t,J=6 Hz), 4.47(2H,q,J=7 Hz), 5.37 and 5.85(2H,ABq,J=14 Hz), 5.38(1H,d,J=5 Hz), 5.90(1H,d,J=5 Hz), 7.83–8.17(1H,m), 8.40–8.93(3H,m).

(2) 7-[2-Ethoxyimino-2-(5-amino-1,2,4-thiadiazol-3-yl)acetamido]-3-[3-(2-dimethylaminoethylthio)-1-pyridiniomethyl]-3-cephem-4-carboxylate (syn isomer). m.p. 105° to 110° C.(dec.).

I.R.(Nujol): 3300, 2690, 2350, 1770, 1665, 1610, 1525 cm$^{-1}$.

N.M.R.(D$_2$O, δ): 1.32(3H,t,J=7 Hz), 2.95(6H,s), 3.53 (4H,s), 3.30 and 3.72(2H,ABq,J=18 Hz), 4.35(2H,q,J=7 Hz), 5.32(1H,d,J=5 Hz), 5.28 and 5.60(2H,ABq,J=14 Hz), 5.85(1H,d,J=5 Hz), 7.87–8.17(1H,m), 8.40–8.65(1H,m), 8.73–8.93(1H,m), 9.17(1H,d,J=2 Hz).

What we claim is:

1. Cephem compounds of the formula:

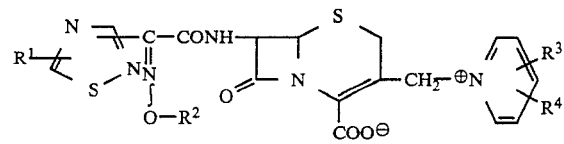

wherein
R$^1$ is amino or a protected amino group;
R$^2$ is lower alkyl which may be substituted with one carboxy, lower alkenyl, lower alkynyl, cyclo (lower) alkyl or cyclo (lower) alkenyl;
R$^3$ is lower alkylamino, N-(lower) alkanoyl (lower) alkylamino, di (lower) alkylamino, sulfo (lower) alkylamino, hydroxy (lower) alkylamino, N-(lower) alkanoylhydroxy (lower) alkylamino, alkanoyloxy (lower) alkyl, alkenoyloxy (lower) alkyl, lower alkoxy (lower) alkoxy (lower) alkyl, di (lower) alkylamino (lower) alkyl, lower alkylthio (lower) alkyl, lower alkylthio, lower alkoxy, lower alkoxy (lower) alkoxy, hydroxy (lower) alkoxy, lower alkanesulfonyl (lower) alkyl, hydroxy (lower) alkylthio, di (lower) alkylamino (lower) alkylthio, tetrazolyl, tetrazolylthio, tetrazolylthio (lower) alkyl or dihydrotriazinylthio (lower) alkyl substituted with oxo, hydroxy and lower alkyl; and R⁴ is hydrogen or lower alkyl; and pharmaceutically acceptable salts thereof.

2. A compound of claim 1, wherein $R^1$ is amino.

3. A compound of the formula:

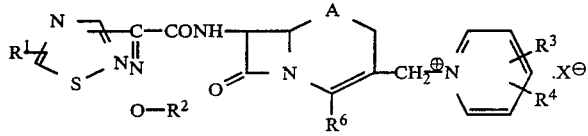

wherein $R^1$ is amino or a protected amino group;

$R^2$ is lower alkyl which may be substituted with one carboxy, lower alkenyl, lower alkynyl, cyclo (lower) alkyl or cyclo (lower) alkenyl;

$R^6$ is a protected carboxy group;

$R^3$ is lower alkylamino, N-(lower) alkanoyl (lower) alkylamino, di (lower) alkylamino, sulfo (lower) alkylamino, hydroxy (lower) alkylamino, N-(lower) alkanoylhydroxy (lower) alkylamino, alkanoyloxy (lower) alkyl, alkenoyloxy (lower) alkyl, lower alkoxy (lower) alkoxy (lower) alkyl, di (lower) alkylamino (lower) alkyl, lower alkylthio (lower) alkyl, lower alkylthio, lower alkoxy, lower alkoxy (lower) alkoxy, hydroxy (lower) alkoxy, lower alkanesulfonyl (lower) alkyl, hydroxy (lower) alkylthio, di (lower) alkylamino (lower) alkylthio, tetrazolyl, tetrazolylthio, tetrazolylthio (lower) alkyl or dihydrotriazinylthio (lower) alkyl substituted with oxo, hydroxy and lower alkyl;

$R^4$ is hydrogen or lower alkyl;

X is an acid residue selected from alkanoyloxy, azido and halogen; and

A is —S— or

and salts thereof.

4. A compound of claim 2, which is 7-[2-ethoxyimino-2-(5-amino-1,2,4-thiadiazol-3-yl)-acetamido]-3-(3-methylamino-1-pyridiniomethyl)-3-cephem-4-carboxylate (syn isomer).

5. A compound of claim 2, which is 7-[2-ethoxyimino-2-(5-amino-1,2,4-thiadiazol-3-yl)-acetamido]-3-(4-methylthio-1-pyridiniomethyl)-3-cephem-4-carboxylate (syn isomer).

6. A compound of claim 2, which is 7-[2-ethoxyimino-2-(5-amino-1,2,4-thiadiazol-3-yl)-acetamido]-3-(3-diethylamino-1-pyridiniomethyl)-3-cephem-4-carboxylate (syn isomer).

7. A compound of claim 2, which is 7-[2-ethoxyimino-2-(5-amino-1,2,4-thiadiazol-3-yl)-acetamido]-3-(3-methylthiomethyl-1-pyridiniomethyl)-3-cephem-4-carboxylate (syn isomer).

8. A compound of claim 2, which is 7-[2-ethoxyimino-2-(5-amino-1,2,4-thiadiazol-3-yl)-acetamido]-3-(3-methoxy-1-pyridiniomethyl)-3-cephem-4-carboxylate (syn isomer).

9. A compound of claim 2, which is sodium 7-[2-ethoxyimino-2-(5-amino-1,2,4-thiadiazol-3-yl)-acetamido]-3-(3-sulfonatomethylamino-1-pyridiniomethyl)-3-cephem-4-carboxylate (syn isomer).

10. A compound of claim 2, which is 7-[2-ethoxyimino-2-(5-amino-1,2,4-thiadiazol-3-yl)-acetamido]-3-[3-(1H-tetrazol-5-ylthiomethyl)-1-pyridiniomethyl]-3-cephem-4-carboxylate (syn isomer).

11. A compound of claim 2, which is 7-[2-ethoxyimino-2-(5-amino-1,2,4-thiadiazol-3-yl)-acetamido]-3-[3-(2-hydroxyethylamino)-1-pyridiniomethyl]-3-cephem-4-carboxylate (syn isomer).

12. A compound of claim 2, which is 7-[2-ethoxyimino-2-(5-amino-1,2,4-thiadiazol-3-yl)-acetamido]-3-[4-(1H-tetrazol-5-yl)-1-pyridiniomethyl)-3-cephem-4-carboxylate (syn isomer).

13. A compound of claim 2, which is 7-[2-(2-cyclopenten-1-yloxyimino)-2-(5-amino-1,2,4-thiadiazol-3-yl)acetamido]-3-[4-(1H-tetrazol-5-yl)-1-pyridiniomethyl]-3-cephem-4-carboxylate (syn isomer).

14. Syn isomer of a compound of claim 1, wherein

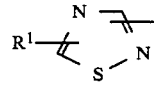

group is

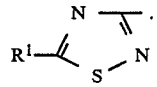

15. A compound of claim 2, wherein $R^2$ is methyl, ethyl, carboxymethyl, allyl, 2-propynyl, cyclopentyl, or 2-cyclopenten-1-yl;

$R^3$ is methylamino, N-formylmethylamino, dimethylamino, sulfomethylamino, 2-hydroxyethylamino, N-formyl-2-hydroxyethylamino, dodecanoyloxymethyl, hexadecanoyloxymethyl, 3-hexadecanoyloxypropyl, oleoyloxymethyl, tetradecanoyloxymethyl, octadecanoyloxymethyl, 2-methoxyethoxymethyl, dimethylaminomethyl, methylthiomethyl, methylthio, methoxy, ethoxy, 2-methoxyethoxy, 2-hydroxyethoxy, mesylmethyl, 2-hydroxyethylthio, 2-dimethylaminoethylthio, 1H-tetrazolyl, 1H-tetrazolylthio, 1H-tetrazolylthiomethyl, or 2-methyl-5-oxo-6-hydroxy-2,5-dihydro-1,2,4-triazinylthiomethyl, and $R^4$ is hydrogen or methyl.

16. A pharmaceutical antibacterial composition comprising an effective amount of a compound of claim 1 in association with a pharmaceutically acceptable, substantially non-toxic carrier or excipient.

* * * * *

UNITED STATES PATENT AND TRADEMARK OFFICE
CERTIFICATE OF CORRECTION

PATENT NO. : 4,521,413

DATED : June 4, 1985

INVENTOR(S) : TSUTOMI TERAJI ET AL

It is certified that error appears in the above-identified patent and that said Letters Patent is hereby corrected as shown below:

Throughout the patent, $$\begin{matrix} C \\ \| \\ N \\ | \\ O-R^2 \end{matrix}$$

should be:

$$\begin{matrix} C \\ \| \\ N \\ \diagdown \\ O-R^2 \end{matrix}.$$

Col. 35, line 5, "1" should be --14--.

Col. 35, lines 48, 52, 56 and 60, "2" should be --15--.

UNITED STATES PATENT AND TRADEMARK OFFICE
CERTIFICATE OF CORRECTION

PATENT NO. : 4,521,413

DATED : June 4, 1985

INVENTOR(S) : TSUTOMI TERAJI ET AL

It is certified that error appears in the above-identified patent and that said Letters Patent is hereby corrected as shown below:

Col. 36, lines 3, 7, 11, 15, 19 and 23,

"2" should be --15--.

Col. 35, line 57, "3-die-" should be --3-dime- --.

Signed and Sealed this

Fifth Day of November 1985

[SEAL]

Attest:

Attesting Officer

DONALD J. QUIGG

Commissioner of Patents and Trademarks